(12) United States Patent
Inui et al.

(10) Patent No.: US 11,359,217 B2
(45) Date of Patent: Jun. 14, 2022

(54) TRANSFORMANT OF CORYNEFORM BACTERIUM AND PRODUCTION METHOD FOR USEFUL COMPOUND USING SAME

(71) Applicant: RESEARCH INSTITUTE OF INNOVATIVE TECHNOLOGY FOR THE EARTH, Kyoto (JP)

(72) Inventors: Masayuki Inui, Kyoto (JP); Kazumi Hiraga, Kyoto (JP); Masako Suda, Kyoto (JP); Takeshi Kubota, Kyoto (JP)

(73) Assignee: RESEARCH INSTITUTE OF INNOVATIVE TECHNOLOGY FOR THE EARTH, Kyoto (JP)

( * ) Notice: Subject to any disclaimer, the term of this patent is extended or adjusted under 35 U.S.C. 154(b) by 0 days.

(21) Appl. No.: 17/051,514

(22) PCT Filed: Feb. 18, 2019

(86) PCT No.: PCT/JP2019/005902
§ 371 (c)(1),
(2) Date: Oct. 29, 2020

(87) PCT Pub. No.: WO2019/211937
PCT Pub. Date: Nov. 7, 2019

(65) Prior Publication Data
US 2021/0222211 A1    Jul. 22, 2021

(30) Foreign Application Priority Data
May 1, 2018    (JP) .............................. JP2018-088424

(51) Int. Cl.
| | | |
|---|---|---|
| C12N 9/88 | (2006.01) | |
| C12P 7/22 | (2006.01) | |
| C12N 9/02 | (2006.01) | |
| C12N 9/10 | (2006.01) | |
| C12R 1/15 | (2006.01) | |

(52) U.S. Cl.
CPC .............. *C12P 7/22* (2013.01); *C12N 9/0069* (2013.01); *C12N 9/1085* (2013.01); *C12N 9/88* (2013.01); *C12Y 113/11001* (2013.01); *C12Y 205/01054* (2013.01); *C12Y 401/01063* (2013.01); *C12Y 402/03004* (2013.01); *C12R 2001/15* (2021.05)

(58) Field of Classification Search
None
See application file for complete search history.

(56) References Cited

U.S. PATENT DOCUMENTS

| | | | |
|---|---|---|---|
| 5,272,073 A | * | 12/1993 | Frost .................... C12N 9/1022 435/155 |
| 5,487,987 A | | 1/1996 | Frost et al. |
| 5,616,496 A | | 4/1997 | Frost et al. |
| 5,629,181 A | | 5/1997 | Frost et al. |
| 8,809,583 B2 | | 8/2014 | Bui et al. |
| 9,453,248 B2 | * | 9/2016 | Yukawa .................. C12N 9/88 |
| 2012/0196339 A1 | | 8/2012 | Koppisch et al. |
| 2013/0030215 A1 | | 1/2013 | Bui et al. |
| 2013/0252294 A1 | | 9/2013 | Koppisch et al. |
| 2015/0203880 A1 | | 7/2015 | Stephanopoulos et al. |
| 2019/0119664 A1 | | 4/2019 | Inui et al. |
| 2019/0194629 A1 | | 6/2019 | Inui et al. |

FOREIGN PATENT DOCUMENTS

| | | |
|---|---|---|
| JP | 9-505463 | 6/1997 |
| JP | 9-506242 | 6/1997 |
| JP | 2013-516196 | 5/2013 |
| WO | 95/07979 | 3/1995 |
| WO | 95/07996 | 3/1995 |
| WO | 2011/085311 | 7/2011 |
| WO | 2012/106257 | 8/2012 |
| WO | 2015/069847 | 5/2015 |
| WO | 2016/207403 | 12/2016 |
| WO | 2017/146241 | 8/2017 |
| WO | 2017/169399 | 10/2017 |

OTHER PUBLICATIONS

International Search Report (ISR) dated May 21, 2019 in International (PCT) Application No. PCT/JP2019/005902.

K.M. Draths et al., "Environmentally Compatible Synthesis of Catechol from D-Glucose", J. Am. Chem. Soc., vol. 117, No. 9, pp. 2395-2400, 1995, cited in the specification.

Victor E. Balderas-Hernandez et al., "Catechol biosynthesis from glucose in *Escherichia coli* anthranilate-overproducer strains by heterologous expression of anthranilate 1,2-dioxygenase from *Pseudomonas aeruginosa* PAO1", Microbial Cell Factories, 13:136, 2014, cited in the specification.

Wensheng Li et al., "Benzene-Free Synthesis of Catechol: Interfacing Microbial and Chemical Catalysis", J. Am. Chem. Soc., vol. 127, No. 9, pp. 2874-2882, 2005, cited in the specification.

Xi-Hui Shen et al., "Genomic Analysis and Identification of Catabolic Pathways for Aromatic Compounds in *Corynebacterium glutamicum*", Microbes and Environments, vol. 20, No. 3, pp. 160-167, 2005, cited in CA.

Xihui Shen et al., "Key enzymes of the protocatechuate branch of the β-ketoadipate pathway for aromatic degradation in *Corynebacterium glutamicum*", Science in China Series C: Life Sciences, vol. 48, No. 3, pp. 241-249, 2005, cited in CA.

Junya Maeda et al., "characterization of phenol 2-monooxygenase from *Corynebacterium glutamicum*", Annual Meeting of the Japan Society for Bioscience, Biotechnology, and Agrochemisty, 2F201, 2016, with machine translation, cited in CA.

(Continued)

*Primary Examiner* — Hope A Robinson

(74) *Attorney, Agent, or Firm* — Wenderoth, Lind & Ponack, L.L.P.

(57) ABSTRACT

Provided is a transformant of a microorganism that has improved catechol productivity.

6 Claims, 1 Drawing Sheet
Specification includes a Sequence Listing.

(56) References Cited

OTHER PUBLICATIONS

Masao Tsuji et al., "Characterization of a Mutant Strain for Catechol Accumulation in *Corynebacterium glutamicum*", J. Ferment. Technol., vol. 54, No. 11, pp. 789-794, 1976, cited in CA.

Extended European Search Report dated Jan. 18, 2022, in Application No. 19796525.4.

Shin et al., "Characterization of a non-phosphotransferase system for cis, cis-muconic acid production in Corynebacterium glutamicum". Biochemical and Biophysical Research Communications, vol. 499, No. 2 (2018), pp. 279-284, cited in CA.

Johnson et al., "Enhancing muconic acid production from glucose and lignin-derived aromatic compounds viz increased protocatechuate decarboxylase activity", Metabolic Engineering Communications, vol. 3, (2016), pp. 111-119, cited in CA.

\* cited by examiner

TRANSFORMANT OF CORYNEFORM BACTERIUM AND PRODUCTION METHOD FOR USEFUL COMPOUND USING SAME

TECHNICAL FIELD

The present disclosure relates to a transformant of a coryneform bacterium. The present disclosure also relates to a method for producing a useful compound (for example, catechol) using the transformant.

BACKGROUND ART

Against the backdrop of global warming and exhaustion of fossil resources, production of chemical products using renewable resources has been recognized to be an important measure with view to realizing a low-carbon society, as new industrial biorefinery, along with biofuel, and has attracted attention.

Catechol is used as a raw material for synthesis of flavoring agents, polymerization inhibitors, antioxidants, pharmaceutical products, and a raw material for synthesis of agricultural chemicals. Catechol is also used as a raw material for removers for a resist (a photosensitive resin applied when a printed substrate is manufactured), deoxygenating agents (activated carbon adsorbents), and plating treatment agents.

Catechol is produced by an oxidation reaction using phenol as a main raw material. However, the production of catechol from renewable resources is earnestly desired, towards the realization of the above-described low-carbon society.

Catechol exists on the metabolic pathway of microorganisms. Catechol is produced through two-stage oxidation of benzene or a decarboxylation reaction with respect to dihydroxybenzoic acid. Thereafter, the decomposition of catechol is promoted through ortho-cleavage or meta-cleavage, and is incorporated in the tricarboxylic acid (TCA) cycle.

Patent Documents 1 and 2 discloses a technique for producing catechol from glucose using a transformed bacterium obtained by using a microorganism of the genus *Escherichia* or the genus *Klebsiella* as a host into which transketolase, DAHP synthase, and 3-dehydroquinate synthase are introduced, and further, dehydroshikimate dehydratase and protocatechuic acid decarboxylase derived from *Klebsiella pneumoniae* are introduced.

The invention disclosed by Patent Document 3 intends to produce adipic acid and cis,cis-muconate using microorganisms. The document, in the discussion, discloses an exemplary production of catechol using the strain having the same configuration as that disclosed in Patent Document 2.

Patent Documents 4 and 5 disclose methods for producing compounds using dehydroshikimic acid as a precursor, and propose a catechol producing method wherein protocatechuic acid decarboxylase derived from *Klebsiella pneumoniae, Enterobacter cloacae, Lactobacillus plantarum*, or *Clostridium butyricum* is caused to express. In the examples disclosed therein, a transformed bacterium obtained by causing 3,4-DHB decarboxylase derived from *Enterobacter cloacae* to express in *Escherichia coli* used.

The invention disclosed by Patent Document 6 intends to produce three types of isomers of muconic acid. The document, in the discussion, discloses an exemplary production of catechol using the strain having the same configuration as that disclosed in Patent Document 2.

Non-Patent Document 1 discloses a technique for producing catechol from glucose using a transformed bacterium obtained by introducing a protocatechuic acid decarboxylase gene of *Klebsiella pneumoniae* into *Escherichia coli*.

Non-Patent Document 2 discloses a technique for producing catechol from glucose using a transformed bacterium obtained by introducing an anthranilate 1,2-dioxygenase gene of *Pseudomonas aeruginosa* into *Escherichia coli*.

Non-Patent Document 3 discloses a technique for producing catechol from glucose using a transformed bacterium obtained by introducing a protocatechuic acid decarboxylase gene of *Klebsiella pneumoniae* into *Escherichia coli*.

PRIOR ART DOCUMENT

Patent Document

Patent Document 1: U.S. Pat. No. 5,272,073
Patent Document 2: JP-T-hei-9(1997)-506242
Patent Document 3: JP-T-hei-9(1997)-505463
Patent Document 4: US Patent No. 2012-0196339
Patent Document 5: US Patent No. 2013-0252294
Patent Document 6: JP-T-2013-516196

Non-Patent Document

Non-Patent Document 1: J. Am. Chem. Soc. (1995) 117: 2395-2400
Non-Patent Document 2: Microb. Cell Fact. (2014) 13:136
Non-Patent Document 3: J. Am. Chem. Soc. (2005) 127: 2874-2882

SUMMARY OF THE INVENTION

Problem to be Solved by the Invention

Regarding the catechol producing method based on a biological method, further improvement in the productivity is expected, toward practical use of the same.

The present disclosure, in one aspect, provides a microorganism that is able to efficiently produce catechol from a saccharide as a raw material, and a method of efficiently producing catechol by using the microorganism.

Means to Solve the Problem

The present disclosure, in one aspect, relates to a transformant of a coryneform bacterium,
wherein the transformant is obtained by introducing, into the coryneform bacterium as a host, at least one gene selected from the group consisting of:
(1) a decarboxylase gene ubiD of *Lactobacillus rhamnosus*;
(2) an ortholog of the gene (1) in at least one of the genus *Lactobacillus*, the genus *Bacillus*, the genus *Enterobacter*, the genus *Escherichia*, the genus *Paenibacillus*, the genus *Citrobacter*, and the genus *Pantoea*; and
(3) a gene in which an enzyme that has an amino acid sequence identity of 70% or more with an amino acid sequence of an enzyme encoded by the gene (1) or (2), and that has a decarboxylation activity, is encoded
wherein a mutation is introduced into a catechol 1,2-dioxygenase gene catA and a protocatechuic acid dehydrogenase gene pcaHG of the coryneform bacterium as a host, and functions of enzymes encoded by the two genes are degraded or lost.

The present disclosure, in another aspect, relates to a catechol producing method that includes:

the step of causing the transformant of a coryneform bacterium according to the present disclosure react in a reaction solution from which at least one of factors necessary for growth, or in a reaction solution under reducing conditions; and the step of collecting catechol in a reaction medium.

Effect of the Invention

According to the present disclosure, in one aspect, the production of catechol in a coryneform bacterium can be made efficient. For example, the production rate and/or yield in the catechol production can be improved.

MODE FOR CARRYING OUT THE INVENTION

Figure 1:
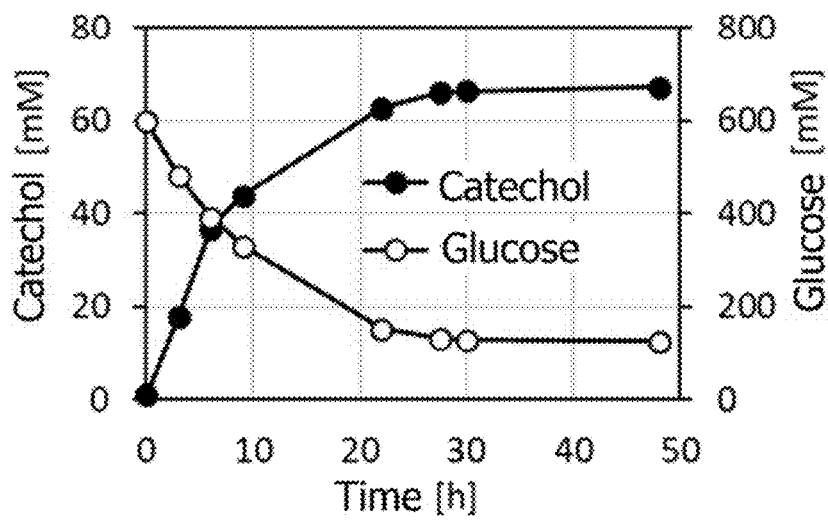
FIG. 1 is a graph showing an exemplary catechol production using a strain CAT21.

As a result of earnest studies, the present inventors found that the catechol productivity can be improved by causing a predetermined decarboxylase to be expressed in a coryneform bacterium into which a mutation that suppresses decomposition of protocatechuic acid and catechol is introduced.

It is estimated that the decarboxylation reaction of protocatechuic acid is accelerated by causing the predetermined decarboxylase to be expressed, whereby the catechol productivity is improved. The present disclosure, however, is not limited to this mechanism.

According to the present disclosure, in one aspect, the production concentration and/or yield of catechol can be improved.

[Host]

In the present disclosure, the host into which a predetermined decarboxylase is introduced is a coryneform bacterium.

In the present disclosure, the coryneform bacteria are a group of microorganisms defined in Bergey's Manual of Determinative Bacteriology Vol. 8, 599 (1974), and are not particularly limited as long as they grow under normal aerobic conditions. The specific examples include bacteria of the genus *Corynebacterium*, bacteria of the genus *Brevibacterium*, bacteria of the genus *Arthrobacter*, bacteria of the genus *Mycobacterium* and bacteria of the genus *Micrococcus* Among the coryneform bacteria, bacteria of the genus *Corynebacterium* are preferred.

Examples of the genus *Corynebacterium* include *Corynebacterium glutamicum, Corynebacterium efficiens, Corynebacterium ammomagenes, Corynebacterium halotolerance*, and *Corynebacterium alkanolyticum*. Among them, *Corynebacterium glutamicum* is preferred for safety and high xylooligosaccharide utilization.

Examples of preferred strains include *Corynebacterium glutamicum* R (FERM P-18976), ATCC13032, ATCC13869, ATCC13058, ATCC13059, ATCC13060, ATCC13232, ATCC13286, ATCC13287, ATCC13655, ATCC13745, ATCC13746, ATCC13761, ATCC14020, ATCC31831, MJ-233 (FERM BP-1497), MJ-233AB-41 (FERM BP-1498). Among them, strains R (FERM P-18976), ATCC13032, and ATCC13869 are preferred.

These strains are available from NBRC (NITE Biological Resource Center), ATCC (American Type Culture Collection), etc., which are microorganism culture collections.

Further, these microorganisms are not only wild strains that exist in the natural world, but may be mutant strains or gene recombinant strains of the same.

With a view to improving the catechol productivity, the transformant according to the present disclosure is configured so that mutations are introduced into the gene catA that encodes an enzyme having a catechol 1,2-dioxygenase activity, and into the gene pcaHG that encodes an enzyme having a protocatechuic acid dehydrogenase activity, in the genome of the coryneform bacterium as a host; and functions of these two enzymes are degraded or lost. Examples of the mutations include substitution, deletion, and insertion of a base sequence.

These mutations may be introduced in advance into a coryneform bacterium to be used as a host, or may be introduced in a process of producing the transformant according to the present disclosure.

Further, with a view to improving the catechol productivity, a gene-modified strain that would improve the production of the protocatechuic acid may be used as a coryneform bacterium as a host (for example, WO2017/169399).

[Introduction of Decarboxylase]

In the present disclosure, a decarboxylase that is introduced into a coryneform bacterium as a host is preferably an enzyme that has a decarboxylation activity with respect to protocatechuic acid.

Examples of the introduction of an enzyme having a decarboxylation activity with respect to protocatechuic acid, into a coryneform bacterium as a host, include the introduction of any one of the following genes (1) to (3) below:

(1) a decarboxylase gene ubiD of *Lactobacillus rhamnosus*;

(2) an ortholog of the gene (1) in the genus *Lactobacillus*, the genus *Bacillus*, the genus *Enterobacter*, the genus *Escherichia*, the genus *Paenibacillus*, the genus *Citrobacter*, and the genus *Pantoea*; and (3) a gene in which an enzyme that has an amino acid sequence identity of 70% or more with an amino acid sequence of an enzyme encoded by the gene (1) or (2), and that has a decarboxylation activity, is encoded.

In the present disclosure, the introduction of the genes (1) to (3) into a host coryneform bacterium can be performed by using a common gene recombination technique (for example, the method proposed by Michael R Green & Joseph Sambrook, "Molecular cloning", Cold spring Harbor Laboratory Press); it can be implemented in the form of the introduction of a gene by using a plasmid vector, or the incorporation of a gene into a host coryneform bacterium chromosome.

In the present disclosure, "incorporating/introducing a gene" refers to incorporating or introducing a gene into a host in such a manner that the gene can express in the host, in one or a plurality of embodiments.

For example, to introduce the ubiDX gene into a host coryneform bacterium, it is preferable to introduce an appropriate promoter in an upstream region on the 5' side of the gene, and it is more preferable to additionally introduce a terminator in a downstream region on the 3' side.

[Decarboxylase Gene ubiD of *Lactobacillus rhamnosus*]

In the present disclosure, a decarboxylase gene ubiD of *Lactobacillus rhamnosus* is registered as LGG_02656 or LGG_RS12695 in a database such as NCBI, in one or a plurality of embodiments.

A decarboxylase gene to be introduced into a host may be an ortholog of the above-described ubiD of *Lactobacillus rhamnosus*. Examples of orthologs of ubiD of *Lactobacillus rhamnosus* include orthologs of the genus *Lactobacillus*, the genus *Bacillus*, the genus *Enterobacter*, the genus *Escherichia*, the genus *Paenibacillus*, the genus *Citrobacter*, and the genus *Pantoea*; with a view to improving the catechol productivity, orthologs of the genus *Lactobacillus*, the genus *Bacillus*, and the genus *Enterobacter* are preferred; among these, orthologs of the genus *Lactobacillus* and the genus *Bacillus* are more preferred; among these, orthologs of the genus *Lactobacillus* are further preferred; and the genes used in Examples are still further preferred.

Examples of the ortholog of the genus *Lactobacillus* for the ubiD gene of *Lactobacillus rhamnosus* include, though not limited to, the ubiD gene of *Lactobacillus pentosus*, the ubiD gene of *Lactobacillus plantarum*, the ubiD gene of *Lactobacillus pobuzihii*, and the ubiD gene of *Lactobacillus composti*.

Examples of the ortholog of the genus *Bacillus* for the ubiD gene of *Lactobacillus rhamnosus* include, though not limited to, the ubiD gene of *Bacillus megaterium*, the ubiD gene of *Bacillus licheniformis*; the ubiD gene of *Bacillus atrophaeus*, the ubiD gene of *Bacillus subtilis* subsp. *subtilis*; and the ubiD gene of *Bacillus subtilis* subsp. *spizizenii*.

Examples of the ortholog of the genus *Enterobacter* for the ubiD gene of *Lactobacillus rhamnosus* include, though not limited to, the ubiD gene of *Enterobacter aerogenes* the ubiD gene of *Enterobacter cloacae*, the ubiD gene of *Enterobacter sakazakii*; and the ubiD gene of *Enterobacter hormaechei*.

Examples of the ortholog of the genus *Escherichia* for the ubiD gene of *Lactobacillus rhamnosus* include, though not limited to, the ubiD gene of *Escherichia coli*, and the ubiD gene of *Escherichia fergusonii*.

Examples of the ortholog of the genus *Paenibacillus* for the ubiD gene of *Lactobacillus rhamnosus* include, though not limited to, the ubiD gene of *Paenibacillus polymyxa*.

Examples of the ortholog of the genus *Citrobacter* for the ubiD gene of *Lactobacillus rhamnosus* include, though not limited to, the ubiD gene of *Citrobacter koseri*.

Examples of the ortholog of the genus *Pantoea* for the ubiD gene of *Lactobacillus rhamnosus* include, though not limited to, the ubiD gene of *Pantoea ananatis*.

It should be noted that the "ortholog gene" in the present disclosure means an analog gene that encodes a protein having a homologous function, existing in a different organism (for example, a different species, a different genus).

A decarboxylase gene to be introduced into a host may be a gene in which an enzyme that has an amino acid sequence identity of 70% or more with an amino acid sequence of an enzyme encoded by the ubiD gene of *Lactobacillus rhamnosus* described above or an ortholog of the same, and that has a decarboxylation activity, is encoded.

The identity of the amino acid sequence is 70% or more, preferably 75% or more, more preferably 80% or more, and further preferably 85% or more, with a view to improving the catechol productivity.

In the present disclosure, it is preferable that, together with the ubiD gene, the ubiX gene, located in the same genome as that of the ubiD gene, is introduced into a host coryneform bacterium together with the ubiD gene, with a view to improving the catechol productivity. Besides, in a case where the ubiH gene is present in the same genome as that of the ubiD gene, it is preferable that the ubiH gene is also introduced into a host coryneform bacterium together with the ubiD gene and the ubiX gene, with a view to improving the catechol productivity.

The ubiD gene and the ubiX gene of *Lactobacillus rhamnosus*, arrayed in this order, constitute an operon, and in such a case, they are described as an ubiDX gene in the present disclosure. In one or a plurality of embodiments, an exemplary base sequence of the ubiDX gene of *Lactobacillus rhamnosus* is the base sequence of SEQ ID NO: 1 in the sequence listing.

In the case where a ubiD gene of *Lactobacillus rhamnosus* is to be introduced into a host coryneform bacterium, the same is preferably introduced as the ubiDX gene of *Lactobacillus rhamnosus*, with a view to improving the catechol productivity. Besides, in the case where an ortholog of a ubiD gene of *Lactobacillus rhamnosus* to be introduced into a host coryneform bacterium, similarly, the ubiX gene and the ubiD gene are preferably introduced into a host coryneform bacterium, with a view to improving the catechol productivity; if there is the ubiH gene in the genome, it is preferable that the ubiH gene, the ubiD gene and the ubiX gene are also introduced into a host coryneform bacterium.

The ubiX gene of *Lactobacillus pentosus*, together with the ubiH gene, constitutes an operon (an ubiHX gene), independently from the ubiD gene. In the case where a ubiD gene of *Lactobacilluspentosus* to be introduced into a host coryneform bacterium, the ubiHX gene and the ubiD gene are preferably introduced, with a view to improving the catechol productivity. In one or a plurality of embodiments, exemplary base sequences of the ubiXH gene and the ubiD gene of *Lactobacillus pentosus* are the base sequences of SEQ ID NOs: 2 and 3 in the sequence listing, respectively.

In the case where a ubiD gene of *Lactobacillus plantarum* is to be introduced into a host coryneform bacterium, similarly, the ubiHX gene and the ubiD gene are preferably introduced therein, with a view to improving the catechol productivity, as is the case with *Lactobacillus pentosus* In one or a plurality of embodiments, exemplary base sequences of the ubiXH gene and the ubiD gene of *Lactobacillus plantarum* are the base sequences of SEQ ID NOs: 4 and 5 in the sequence listing, respectively.

In the case where the ubiD gene of *Lactobacillus pobuzihii* or that of *Lactobacillus composti*, is to be introduced into a host coryneform bacterium, similarly, it is preferably introduced as the ubiDX gene of *Lactobacillus pobuzihii* or *Lactobacillus composti*, with a view to improving the catechol productivity. In one or a plurality of embodiments, exemplary base sequences of the ubiDX gene of *Lactobacillus pobuzihii* and *Lactobacillus composti* are the base sequences of SEQ ID NOs: 6 and 7 in the sequence listing.

Regarding the ubiD gene of *Bacillus megaterium*, the ubiX gene, the ubiD gene, and the ubiH gene, arrayed in this order, constitute an operon, and in such a case, they are described as an ubiXDH gene in the present disclosure. In the case where the ubiD gene of *Bacillus megaterium* is to be introduced into a host coryneform bacterium, the same is preferably introduced as the ubiXDH gene, with a view to improving the catechol productivity. In one or a plurality of embodiments, an exemplary base sequence of the ubiXDH gene of *Bacillus megaterium* is the base sequence of SEQ ID NO: 10 in the sequence listing.

In the case where the ubiD gene of *Bacillus licheniformis* is to be introduced into a host coryneform bacterium, the same is preferably introduced as the ubiXDH gene, with a view to improving the catechol productivity. In one or a plurality of embodiments, an exemplary base sequence of the ubiXDH gene of *Bacillus licheniformis* is the base sequence of SEQ ID NO: 11 in the sequence listing.

In the case where the ubiD gene of *Bacillus atrophaeus* is to be introduced into a host coryneform bacterium, the same is preferably introduced as the ubiXDH gene, with a view to improving the catechol productivity. In one or a plurality of embodiments, an exemplary base sequence of the ubiXDH gene of *Bacillus atrophaeus* is the base sequence of SEQ ID NO: 12 in the sequence listing.

In the case where the ubiD gene of *Bacillus subtilis* subsp. *subtilis* is to be introduced into a host coryneform bacterium, the same is preferably introduced as the ubiXDH gene, with a view to improving the catechol productivity. In one or a plurality of embodiments, an exemplary base sequence of the ubiXDH gene of *Bacillus subtilis* subsp. *subtilis* is the base sequence of SEQ ID NO: 13 in the sequence listing.

In the case where the ubiD gene of *Bacillus subtilis* subsp. *spizizenii* is to be introduced into a host coryneform bacterium, the same is preferably introduced as the ubiXDH gene, with a view to improving the catechol productivity. In one or a plurality of embodiments, an exemplary base sequence of the ubiXDH gene of *Bacillus subtilis* subsp. *spizizenii* is the base sequence of SEQ ID NO: 14 in the sequence listing.

In the case where the ubiD gene of *Enterobacter aerogenes* is to be introduced into a host coryneform bacterium, the same is preferably introduced as the ubiXDH gene, with a view to improving the catechol productivity. In one or a plurality of embodiments, an exemplary base sequence of the ubiXDH gene of *Enterobacter aerogenes* is the base sequence of SEQ ID NO: 15 in the sequence listing.

In the case where the ubiD gene of *Enterobacter cloacae* is to be introduced into a host coryneform bacterium, the same is preferably introduced as the ubiXDH gene, with a view to improving the catechol productivity. In one or a plurality of embodiments, an exemplary base sequence of the ubiXDH gene of *Enterobacter cloacae* is the base sequence of SEQ ID NO: 16 in the sequence listing.

In the case where the ubiD gene of *Enterobacter sakazakii* is to be introduced into a host coryneform bacterium, the same is preferably introduced as the ubiXDH gene, with a view to improving the catechol productivity. In one or a plurality of embodiments, an exemplary base sequence of the ubiXDH gene of *Enterobacter sakazakii* is the base sequence of SEQ ID NO: 17 in the sequence listing.

In the case where the ubiD gene of *Enterobacter hormaechei* is to be introduced into a host coryneform bacterium, the same is preferably introduced in the form of the ubiXDH gene, with a view to improving the catechol productivity. In one or a plurality of embodiments, an exemplary base sequence of the ubiXDH gene of *Enterobacter hormaechei* is the base sequence of SEQ ID NO: 18 in the sequence listing.

In the case where the ubiD gene of *Escherichia coli* W is to be introduced into a host coryneform bacterium, the same is preferably introduced as the ubiXDH gene, with a view to improving the catechol productivity. In one or a plurality of embodiments, an exemplary base sequence of the ubiXDH gene of *Escherichia coli* W is the base sequence of SEQ ID NO: 19 in the sequence listing.

In the case where the ubiD gene of *Escherichia fergusonii* is to be introduced into a host coryneform bacterium, the same is preferably introduced as the ubiXDH gene, with a view to improving the catechol productivity. In one or a plurality of embodiments, an exemplary base sequence of the ubiXDH gene of *Escherichia fergusonii* is the base sequence of SEQ ID NO: 20 in the sequence listing.

In the case where the ubiD gene of *Paenibacillus polymyxa* is to be introduced into a host coryneform bacterium, the same is preferably introduced as the ubiXDH gene, with a view to improving the catechol productivity. In one or a plurality of embodiments, an exemplary base sequence of the ubiXDH gene of *Paenibacillus polymyxa* is the base sequence of SEQ ID NO: 21 in the sequence listing.

In the case where the ubiD gene of *Citrobacter koseri* is to be introduced into a host coryneform bacterium, the same is preferably introduced as the ubiXDH gene, with a view to improving the catechol productivity. In one or a plurality of embodiments, an exemplary base sequence of the ubiXDH gene of *Citrobacter koseri* is the base sequence of SEQ ID NO: 22 in the sequence listing.

In the case where the ubiD gene of *Pantoea ananatis* is to be introduced into a host coryneform bacterium, the same is preferably introduced as the ubiXDH gene, with a view to improving the catechol productivity. In one or a plurality of embodiments, an exemplary base sequence of the ubiXDH gene of *Pantoea ananatis* is the base sequence of SEQ ID NO: 23 in the sequence listing.

[Transformant]

The present disclosure, in one aspect, relates to a transformant obtained by introducing any one of the above-described genes (1) to (3) into a host coryneform bacterium, wherein functions of two enzymes in the host genome, which are catechol 1,2-dioxygenase (catA) and protocatechuic acid dehydrogenase (pcaHG), are degraded or lost.

The transformant according to the present disclosure, in one or a plurality of embodiments, is capable of efficiently producing catechol.

In the transformant according to the present disclosure, in one or a plurality of embodiments, the ubiX gene and/or the ubiH gene are preferably introduced, with a view to improving the catechol productivity.

The transformant according to the present disclosure may be further characterized in that another gene (or genes) is introduced therein, or that a gene (or genes) is deleted and/or mutated, to produce catechol or to make the production more efficient.

In one or a plurality of embodiments for making the production of catechol more efficient, the introduction or disruption of a gene for improving the production of protocatechuic acid is performed, for example. Exemplary introduction of a gene for improving the production of protocatechuic acid is the introduction of a gene that encodes an enzyme having 3-deoxy-D-arabino-heptulosonate-7-phosphate synthase activity (for example, aroG), and/or a gene that encodes an enzyme having 3-dehydroquinate synthase activity (for example, qsuB).

The transformant according to the present disclosure, in one or a plurality of embodiments, can be used in the production of catechol. The transformant according to the present disclosure, in one or a plurality of embodiments, can be used in the production of an organic compound from catechol as an intermediate.

[Method for Producing Catechol]

The transformant according to the present disclosure is capable of producing catechol at a high efficiency in a reaction solution without bacterial cell growth, using saccharides as raw materials.

The present disclosure, therefore, in another aspect, relates to a catechol producing method that includes the steps of causing the transformant of the coryneform bacterium according to the present disclosure to react in a reaction solution in which at least one of factors necessary for growth is removed, or in a reaction solution under reducing conditions; and collecting catechol in a reaction medium.

In the catechol producing method according to the present invention, first of all, the above-described transformant according to the present disclosure is cultured to grow under aerobic conditions.

The transformant according to the present disclosure can be cultured by using a normal nutrient medium that contains a carbon source, a nitrogen source, inorganic salts, and the like. In the culture, as a carbon source, for example, glucose, waste molasses, or the like can be used alone or in mixture, and as a nitrogen source, for example, ammonium, ammonium sulfate, ammonium chloride, ammonium nitrate, urea, or the like can be used alone or in mixture. Further, as an inorganic salt, for example, dibasic potassium phosphate, potassium dihydrogen phosphate, magnesium sulfate, or the like can be used. In addition to these, nutrients such as peptone, meat extract, yeast extract, corn steep liquor, various types of vitamins such as casamino acid, biotin, or thiamine can be appropriately added to the medium as required.

Generally, the culturing can be carried out under aerobic conditions such as aeration stirring or shaking, at a temperature of about 20° C. to about 60° C., preferably about 25° C. to about 35° C. The pH during the culturing is in a range of, for example, around 5 to 10, preferably around 7 to 8, and the pH adjustment during the culturing can be carried out by adding acid or alkali. The carbon source concentration at the start of the culturing is about 1% (W/V) to about 20% (W/V), preferably about 2% (W/V) to about 5% (W/V). Further, the culturing period is usually about 1 to 7 days.

Next, cultured bacterial cells of the transformant according to the present disclosure are collected. A method for collecting and separating cultured bacterial cells from the cultured substance thus obtained as described above is not limited particularly, and a known method such as centrifugation or membrane separation can be used, for example.

The cultured bacterial cells thus collected may be processed, and the processed bacterial cells thus obtained may be used in the next step. Examples of the processed bacterial cells include cultured bacterial cells subjected to a certain processing operation, for example, immobilized bacterial cells that are obtained by immobilizing bacterial cells with acrylamide, carrageenan, or the like.

In the catechol production reaction by the cultured bacterial cells of the transformant according to the present disclosure, collected and separated from the cultured substance thus obtained as described above, or by the processed bacterial cells obtained from the same, any production process under aerobic conditions or reducing conditions may be used, as long as it is in a solution of a reaction without bacterial cell growth. The catechol production process may be of a batch type, or of a continuous type.

In the present disclosure, "does not grow" encompasses "substantially does not grow", and "hardly grows". For example, in a reaction under aerobic conditions, growth of the transformant can be avoided or inhibited by the use of a reaction solution in which one or more of compounds essential for the growth of the microorganism, for example, vitamins, such as biotin and thiamine, nitrogen sources, etc. is depleted or limited.

Besides, under reducing conditions, coryneform bacteria substantially do not grow, and therefore, the composition of the reaction solution is not limited. The oxidation-reduction potential of the reaction solution under reducing conditions is preferably about-200 mV to about −500 mV, and more preferably about −150 mV to −500 mV. The reduced state of the reaction solution can be simply estimated using a resazurin indicator (in a reduced state, decolorization from blue to colorless is observed). However, for precise measurement, a redox-potential meter (for example, ORP Electrodes made by BROADLEY JAMES) may be used.

In the present disclosure, it is preferable that reducing conditions are maintained immediately after bacterial cells or processed bacterial cells are added to a reaction solution until catechol is collected; however, a reaction solution may be in a reduced state at least at the point in time when catechol is collected. It is desirable that a reaction solution is kept under reducing conditions during about 50% or more of a reaction period, preferably during about 70% or more of the same, and more preferably during about 90% or more of the same. Particularly, it is more desirable that a reaction solution has an oxidation-reduction potential kept at about −200 mV to about −500 mV during about 50% or more of a reaction period, preferably during about 70% or more of the same, and more preferably during about 90% or more of the same.

The reaction solution contains an organic carbon source (for example, saccharides) that are raw materials used in the production of catechol. Examples of the organic carbon source include materials that the transformant according to the present disclosure can utilize in a biochemical reaction. Specifically, examples of saccharides include monosaccharides, such as glucose, xylose, arabinose, galactose, fructose, and mannose; disaccharides, such as cellobiose, sucrose, lactose, and maltose; and polysaccharides, such as dextrin and soluble starch; etc. Among these, glucose is preferable.

The present disclosure, therefore, in one aspect, relates to a catechol producing method that includes the steps of causing the transformant of the coryneform bacterium according to the present disclosure to react in a reaction solution in which at least one of factors necessary for growth is removed, or in a reaction solution under reducing conditions; and collecting catechol in a reaction medium.

Finally, the catechol produced in the reaction medium as described above is collected. For doing so, a known method that is used in bioprocessing can be used. Examples of such a known method include the salting-out method, the recrystallization method, the organic solvent extraction method, the distillation method (reactive distillation by esterification etc.), the chromatography separation method, and the electrodialysis method, which can be used with respect to a solution of catechol. The method for separating and purifying catechol may be decided appropriately.

The present disclosure relates to the following, in one or a plurality of embodiments:

[1] A transformant of a coryneform bacterium that is obtained by introducing, into the coryneform bacterium as a host, at least one gene selected from the group consisting of:

(1) a decarboxylase gene ubiD of *Lactobacillus rhamnosus*;

(2) an ortholog of the gene (1) in at least one of the genus *Lactobacillus*, the genus *Bacillus*, the genus *Enterobacter*, the genus *Escherichia*, the genus *Paenibacillus*, the genus *Citrobacter*, or the genus *Pantoea*; and (3) a gene in which an enzyme that has an amino acid sequence identity of 70% or more with an amino acid sequence of an enzyme encoded by the gene (1) or (2), and that has a decarboxylation activity, is encoded.

wherein mutations are introduced into a catechol 1,2-dioxygenase gene catA, and a protocatechuic acid dehydrogenase gene pcaHG in the coryneform bacterium as a host; and functions of enzymes encoded by the gene catA and functions of enzymes encoded by the gene pcaHG are degraded or lost.

[2] The transformant according to Item [1],
wherein the transformant has a catechol producing ability.

[3] The transformant according to Item [1] or [2],
wherein at least one of a gene that encodes an enzyme having 3-deoxy-D-arabino-heptulosonate-7-phosphate synthase activity, and a gene that encodes an enzyme having 3-dehydroquinate synthase activity, is additionally introduced.

[4] The transformant according to any one of Items [1] to [3],
wherein the coryneform bacterium as a host is *Corynebacterium glutamicum*.

[5] The transformant according to any one of Items [1] to [4],
wherein the coryneform bacterium as a host is *Corynebacterium glutamicum* R (FERM P-18976), ATCC13032, or ATCC13869.

[6] A transformant of *Corynebacterium glutamicum* CAT21 (Accession Number: NITE BP-02689).

[7] A catechol producing method including the steps of
causing the transformant of a coryneform bacterium according to any one of Items [1] to [6] to react in a reaction solution in which at least one of factors necessary for growth is removed, or in a reaction solution under reducing conditions; and
collecting catechol in a reaction medium.

[8] The catechol producing method according to Item [7],
wherein, in the reaction solution, at least one saccharide selected from the group consisting of glucose, fructose, cellobiose, xylobiose, sucrose, lactose, maltose, dextrin, xylose, arabinose, galactose, mannose, and soluble starch is converted into catechol with use of the transformant according to any one of Items [1] to [6], and catechol is collected from the reaction solution.

EXAMPLE

The following description describes the present invention in detail, while referring to examples, but the present invention is not limited to these examples.

Example 1

Construction of Catechol Producing Strain
(1) Preparation/Obtainment of Chromosomal DNA

*Corynebacterium glutamicum* R(FERM P-18976), *Lactobacillus rhamnosus* NBRC 3425, *Lactobacillus pentosus* JCM 1558, *Lactobacillus plantarum* NBRC 3070, *Lactobacillus pobuzihii* JCM 18084, *Lactobacillus composti* JCM 14202, *Lactobacillus hokkaidonensis* JCM 18461, *Lactobacillus sakei* subsp. *sakei* JCM 1157, *Bacillus megaterium* JCM 2506, *Bacillus licheniformis* JCM 2505, *Bacillus atrophaeus* JCM 9070, *Bacillus subtilis* subsp. *subtilis* NBRC 14144, *Bacillus subtilis* subsp. *spizizenii* NBRC 101239, *Enterobacter aerogenes* NBRC 13534, *Enterobacter cloacae* NBRC 13535, *Enterobacter hormaechei* ATCC 49162, *Escherichia coli* W NBRC 13500, *Escherichia fergusonii* NBRC 102419, *Paenibacillus polymyxa* NBRC 15309, and *Pantoea ananatis* LMG 20103 were cultured according to information obtained from organizations from which the strains are available, and thereafter, chromosomal DNAs thereof were prepared by using DNA genome extraction kit (trade name: "GenomicPrep Cells and Tissue DNA Isolation Kit", manufactured by Amersham PLC). Chromosomal DNAs of *Enterobacter sakazakii* ATCC BAA-894D-5 and *Citrobacter koseri* ATCC BAA-895D-5 were obtained from ATCC.

(2) Construction of Plasmid for Expression of Catechol-Production-Related Gene

Primer sequences used for isolating target enzyme genes are shown in Table 1. In PCR, Veriti Thermal Cycler (manufactured by Applied Biosystems Inc.) was used, and PrimeSTAR HS DNA Polymerase (manufactured by Takara Bio Inc.) was used as a reaction reagent.

DNA fragments obtained were introduced into cloning vectors containing PgapApromoters (pCRB209 [WO2012/033112], pCRB210 [WO2012/033112]). It should be noted that in *Lactobacillus pentosus* and those of *Lactobacillus plantarum*, the ubiD gene and the ubiXH gene are located at different positions on the chromosome, and therefore they were separately cloned, and then transferred onto the same plasmid.

The names of the cloning vectors introduced and the plasmids obtained are shown in Table 2.

TABLE 1

Primer for Isolation of Catechol-Production-Related Gene

| Gene Source | Enzyme Gene | Forward | Reverse | Gene Sequence |
|---|---|---|---|---|
| Lactobacillus rhamnosus | ubiDX | SEQ ID NO. 24 | SEQ ID NO. 25 | SEQ ID NO. 1 |
| Lactobacillus pentosus | ubiXH | SEQ ID NO. 26 | SEQ ID NO. 27 | SEQ ID NO. 2 |
| Lactobacillus pentosus | ubiD | SEQ ID NO. 28 | SEQ ID NO. 29 | SEQ ID NO. 3 |
| Lactobacillus plantarum | ubiXH | SEQ ID NO. 30 | SEQ ID NO. 31 | SEQ ID NO. 4 |
| Lactobacillus plantarum | ubiD | SEQ ID NO. 32 | SEQ ID NO. 33 | SEQ ID NO. 5 |
| Lactobacillus pobuzihii | ubiDX | SEQ ID NO. 34 | SEQ ID NO. 35 | SEQ ID NO. 6 |
| Lactobacillus composti | ubiDX | SEQ ID NO. 36 | SEQ ID NO. 37 | SEQ ID NO. 7 |
| Lactobacillus hokkaidonensis | ubiDXH | SEQ ID NO. 38 | SEQ ID NO. 39 | SEQ ID NO. 8 |
| Lactobacillus sakei subsp. sakei | ubiDXH | SEQ ID NO. 40 | SEQ ID NO. 41 | SEQ ID NO. 9 |
| Bacillus megaterium | ubiXDH | SEQ ID NO. 42 | SEQ ID NO. 43 | SEQ ID NO. 10 |
| Bacillus licheniformis | ubiXDH | SEQ ID NO. 44 | SEQ ID NO. 45 | SEQ ID NO. 11 |
| Bacillus atrophaeus | ubiXDH | SEQ ID NO. 46 | SEQ ID NO. 47 | SEQ ID NO. 12 |
| Bacillus subtilis subsp. subtilis | ubiXDH | SEQ ID NO. 48 | SEQ ID NO. 49 | SEQ ID NO. 13 |
| Bacillus subtilis subsp. spizizenii | ubiXDH | SEQ ID NO. 50 | SEQ ID NO. 51 | SEQ ID NO. 14 |
| Enterobacter aerogenes | ubiXDH | SEQ ID NO. 52 | SEQ ID NO. 53 | SEQ ID NO. 15 |
| Enterobacter cloacae | ubiXDH | SEQ ID NO. 54 | SEQ ID NO. 55 | SEQ ID NO. 16 |
| Enterobacter sakazakii | ubiXDH | SEQ ID NO. 56 | SEQ ID NO. 57 | SEQ ID NO. 17 |
| Enterobacter hormaechei | ubiXDH | SEQ ID NO. 58 | SEQ ID NO. 59 | SEQ ID NO. 18 |

TABLE 1-continued

Primer for Isolation of Catechol-Production-Related Gene

| Gene Source | Enzyme Gene | Forward | Reverse | Gene Sequence |
|---|---|---|---|---|
| Escherichia coli W | ubiXDH | SEQ ID NO. 60 | SEQ ID NO. 61 | SEQ ID NO. 19 |
| Escherichia fergusonii | ubiXDH | SEQ ID NO. 62 | SEQ ID NO. 63 | SEQ ID NO. 20 |
| Paenibacillus polymyxa | ubiXDH | SEQ ID NO. 64 | SEQ ID NO. 65 | SEQ ID NO. 21 |
| Citrobacter koseri | ubiXDH | SEQ ID NO. 66 | SEQ ID NO. 67 | SEQ ID NO. 22 |
| Pantoea ananatis | ubiXDH | SEQ ID NO. 68 | SEQ ID NO. 69 | SEQ ID NO. 23 |

TABLE 2

Plasmid for Expression of Catechol-Production-Related Gene

| Gene Source | Enzyme Gene | Introduced Vector | Plasmid |
|---|---|---|---|
| Lactobacillus rhamnosus | ubiDX | pCRB209 | Pani37 |
| Lactobacillus pentosus | ubiXH | pCRB209 | Pani277 |
| Lactobacillus pentosus | ubiD | pCRB209 | Pani278 |
| Lactobacillus pentosus | ubiXH + ubiD | Pani277 | Pani279 |
| Lactobacillus plantarum | ubiXH | pCRB209 | Pani33 |
| Lactobacillus plantarum | ubiD | pCRB209 | Pani34 |
| Lactobacillus plantarum | ubiXH + ubiD | Pani33 | Pani40 |
| Lactobacillus pobuzihii | ubiDX | pCRB209 | Pani284 |
| Lactobacillus composti | ubiDX | pCRB209 | Pani283 |
| Lactobacillus hokkaidonensis | ubiDXH | pCRB210 | Pani282 |
| Lactobacillus sakei subsp. sakei | ubiDXH | pCRB210 | Pani281 |
| Bacillus megaterium | ubiXDH | pCRB209 | PGadi21 |
| Bacillus licheniformis | ubiXDH | pCRB209 | PGadi20 |
| Bacillus atrophaeus | ubiXDH | pCRB209 | Pani63 |
| Bacillus subtilis subsp. subtilis | ubiXDH | pCRB209 | pCRG34 |
| Bacillus subtilis subsp. spizizenii | ubiXDH | pCRB209 | Pani60 |
| Enterobacter aerogenes | ubiXDH | PCRB209 | Pani86 |
| Enterobacter cloacae | ubiXDH | pCRB209 | Pani26 |
| Enterobacter sakazakii | ubiXDH | pCRB209 | Pani81 |
| Enterobacter hormaechei | ubiXDH | pCRB209 | Pani88 |
| Escherichia coli W | ubiXDH | pCRB209 | Pani80 |
| Escherichia fergusonii | ubiXDH | PCRB209 | Pani85 |
| Paenibacillus polymyxa | ubiXDH | PCRB209 | Pani84 |
| Citrobacter koseri | ubiXDH | pCRB209 | Pani83 |
| Pantoea ananatis | ubiXDH | pCRB209 | Pani82 |

(3) Construction of Plasmid for Chromosomal Gene Disruption of *Corynebacterium Glutamicum* Strain R A DNA region necessary for markerless chromosomal gene disruption of a *Corynebacterium glutamicum* strain R was amplified by the PCR method. Each PCR fragment is linkable in overlap regions. The DNA fragment thus obtained was introduced into the plasmid pCRA725 [J. Mol. Microbiol. Biotechnol. 8: 243-254 (2004), (JP-A-2006-124440)] for markerless gene disruption. Obtained plasmids for chromosome gene disruption are shown in Table 3.

TABLE 3

Plasmid for Chromosomal Gene Disruption of *Corynebacterium Glutamicum* Strain R

| Plasmid for Chromosomal Disruption | Disruptied Gene | Forward | Reverse |
|---|---|---|---|
| pCRG33 | catA | SEQ ID NO. 70 | SEQ ID NO. 71* |
|  |  | SEQ ID NO. 72* | SEQ ID NO. 73 |

*Primer including overlap region (4) Construction of Catechol Producing Strains by Chromosomal Gene Recombination The vector pCRA725 for markerless chromosomal gene introduction is a plasmid that cannot be replicated in *Corynebacterium glutamicum* R. In a case of a single crossover strain that has a crossover with the homologous region on the chromosome introduced into the plasmid pCRA725, the strain exhibits the kanamycin resistance due to the expression of the kanamycin-resistant gene on pCRA725, and the lethality in a sucrose-containing medium due to the expression of the sacR-sacB gene of the *Bacillus subtilis*. In contrast, in a case of a double crossover strain, the strain exhibits the kanamycin sensitivity due to the loss of the kanamycin-resistant gene on pCRA725, and the viability in a sucrose-containing medium due to the loss of the sacR-sacB gene. A markerless chromosomal gene introduced strain, therefore, exhibits the kanamycin sensitivity and the viability in the sucrose-containing medium.

By the above-described methods, PCA-production-related gene chromosome integrated strains were constructed by using the above-described plasmids for catechol-production-related gene chromosomal integration and the plasmids for chromosomal genes disruption. A *Corynebacterium glutamicum* strain PCA3 [WO2017/169399], which is a coryneform bacterium that produces protocatechuic acid, was used as a host strain. Further, the plasmid pCRG3 [WO2017/169399] for gene pcaHG disruption, the plasmid pCRB295 [WO2017/169399] for the qsuB gene chromosome integration, and the plasmid pCRB285 [WO2017/169399] for the aroG gene (S180F) chromosome integration were also used. This chromosomal gene recombination is outlined in Tables 4 and 5.

TABLE 4

Construction of Catechol Producing Strains by Chromosomal Gene Recombination

| Constructed Strain | Host Strain | Recombinant Plasmid |
|---|---|---|
| LHglc1367 | Corynebacterium glutamicum PCA3 | pCRG33 |
| ESglc1590 | Corynebacterium glutamicum R | pCRG33, pCRG3 |
| ESglc1609 | ESglc1590 | PCRB295, pCRB285 |

TABLE 5

Outline of Strain Constructed by Chromosomal Gene Recombination

| Constructed Strain | Chromosome integrated gene | Disrupted chromosomal gene |
|---|---|---|
| LHglc1367 | xylABx4, bglF(V317A)A, araBAD, araE, tkt-tal, aroG(S180F)x2, aroCKBx3, aroAx2, aroDx2, aroEx2, qsuB, pobAx2, ubiC | qsuD, poxF, pcaHG, catA, ldhA |
| ESglc1590 |  | pcaHG, catA |
| ESglc1609 | qsuB, aroG(S180F) | pcaHG, catA | x2, x3: indicating the number of genes introduced into chromosome (5) Construction of Strain in which Plasmid for Expression of Catechol-Producing Gene is Introduced Catechol-producing strains were constructed by introducing a protocatechuic acid decarboxylase into the above-described chromosomal gene recombinant strains. Besides, pCRB22 (Appl Microbiol Biotechnol. 2015 June; 99(11): 4679-89) was used for carrying out control experiments. The strains thus constructed are outlined in Table 6.

TABLE 6

Outline of Catechol Producing Strain

| Constructed Strain | Host Strain | Introduced Plasmid | Source of Protocatechuic Acid Decarboxylase Gene |
|---|---|---|---|
| CAT21 | LHglc1367 | Pani37 | Lactobacillus rhamnosus |
| CAT41 | LHglc1367 | Pani279 | Lactobacillus pentosus |
| CAT24 | LHglc1367 | Pani40 | Lactobacillus plantarum |
| CAT42 | LHglc1367 | Pani284 | Lactobacillus pobuzihii |
| CAT45 | LHglc1367 | Pani283 | Lactobacillus composti |
| CAT6 | LHglc1367 | PGadi21 | Bacillus megaterium |
| CAT5 | LHglc1367 | PGadi20 | Bacillus licheniformis |
| CAT39 | LHglc1367 | Pani63 | Bacillus atrophaeus |
| CAT2 | LHglc1367 | pCRG34 | Bacillus subtilis subsp. subtilis |
| CAT38 | LHglc1367 | Pani60 | Bacillus subtilis subsp. spizizenii |
| CAT37 | LHglc1367 | Pani86 | Enterobacter aerogenes |
| CAT1 | LHglc1367 | Pani26 | Enterobacter cloacae |
| CAT32 | LHglc1367 | Pani81 | Enterobacter sakazakii |
| CAT40 | LHglc1367 | Pani88 | Enterobactor hormaechei |
| CAT31 | LHglc1367 | Pani80 | Escherichia coli W |
| CAT36 | LHglc1367 | Pani85 | Escherichia fergusonii |
| CAT35 | LHglc1367 | Pani84 | Paenibacillus polymyxa |
| CAT34 | LHglc1367 | Pani83 | Citrobacter koseri |
| CAT33 | LHglc1367 | Pani82 | Pantoea ananatis |
| CAT158 | LHglc1367 | pCRB22 | — |
| CAT91 | ESglc1590 | Pani37 | Lactobacillus rhamnosus |
| CAT92 | ESglc1609 | Pani37 | Lactobacillus rhamnosus |

*Corynebacterium glutamicum* CAT21 was deposited in Incorporated Administrative Agency National institute of Technology and Evaluation, NITE Patent Microorganisms Depositary (2-5-8-122 Kazusakamatari, Kisarazu-shi, Chiba 292-0818 Japan) as an international depositary authority (International deposit date: Apr. 17, 2018, Accession Number: NITE BP-02689 under the Budapest Treaty).

Example 21

Catechol Production Test (in Test Tube, 10 mL Scale) (Combination of Protocatechuic Acid Decomposition Pathway Disruption, Catechol Decomposition Pathway Disruption)

By using a strain CAT91, which is a catechol producing strain, which was constructed on the basis of a *Corynebacterium glutamicum* strain R (see Tables 5 and 6), experiments of producing catechol in an aerobic batch reaction using a test tube were carried out by the method described below.

Each strain CAT91 was applied to A-agar plate [obtained by dissolving the following in 1 liter of distilled water: $(NH_2)_2CO$ 2 g; $(NH_4)_2SO_4$ 7 g; $KH_2PO_4$ 0.5 g; $K_2HPO4$ 0.5 g; $MgSO_4.7H_2O$ 0.5 g; 0.06% (w/v) $FeSO_4.7H_2O$, 0.042% (w/v) $MnSO_4.2H_2O$ 1 ml; 0.02% (w/v) biotin solution 1 ml; 0.01% (w/v) thiamin solution 2 ml; yeast extract 2 g; vitamin assay casamino acid 7 g; and agar 15 g] containing kanamycin of final concentration 50 µg/mL and 4% glucose, and it was incubated at 33° C. for 15 hours in a dark place.

One platinum loop of the strain CAT91 grown on the above-described plate was inoculated in a test tube containing 10 ml of A-liquid medium [obtained by dissolving the following in 1 liter of distilled water: $(NH_2)_2CO$ 2 g; $(NH_4)_2SO_4$ 7 g; $KH_2PO_4$ 0.5 g; $K_2HPO_4$ 0.5 g; $MgSO_4.7H_2O$ 0.5 g; 0.06% (w/v) $FeSO_4.7H_2O$, 0.042% (w/v) $MnSO_4.2H_2O$ 1 ml; 0.02% (w/v) biotin solution 1 ml; 0.01% (w/v) thiamin solution 2 ml; yeast extract 2 g; and vitamin assay casamino acid 7 g] containing kanamycin of final concentration 50 µg/mL and 2% glucose, and aerobic shaking culture was carried out at 33° C. for 7 to 15 hours.

Each strain grown under the above-described conditions was suspended in 10 ml of A-liquid medium containing kanamycin of final concentration 50 µg/mL and 4% glucose so that the initial bacterial cell concentration $OD_{610}$=0.5. 200 mg of $CaCO_3$ was added thereto and aerobic shaking culture was carried out at 33° C. for 48 hours. The culture solution obtained after 48 hours was centrifuged (4° C., 15,000×g, 5 minutes), whereby supernatant of culture was obtained. The concentration of metabolite in the supernatant of culture was analyzed by using a high-performance liquid chromatography system (Prominence HPLC (manufactured by Shimadzu Corporation), COSMOSIL Packed column 5C18-AR-II, separation using 10% methanol and 0.1% phosphoric acid for the mobile phase). Consequently, this strain produced 0.1 mM of catechol after 48 hours.

Example 31

Catechol Production Test (in Test Tube, 10 mL Scale) (Combination of Protocatechuic Acid Decomposition Pathway Disruption, Catechol Decomposition Pathway Disruption, DAHP Synthesis Enzyme Reinforcement, and Protocatechuic Acid Synthesis Enzyme Reinforcement)

By using the strain CAT92, which is a catechol producing strain constructed on the basis of the strain CAT91 (see Tables 5 and 6)), experiments of producing catechol in an aerobic batch reaction using a test tube were carried out by the method described below.

Each strain CAT92 was applied to A-agar plate [obtained by dissolving the following in 1 liter of distilled water: $(NH_2)_2CO$ 2 g; $(NH_4)_2SO_4$ 7 g; $KH_2PO_4$ 0.5 g; $K_2HPO_4$ 0.5 g; $MgSO_4.7H_2O$ 0.5 g; 0.06% (w/v) $FeSO_4.7H_2O$+0.042% (w/v) $MnSO_4.2H_2O$ 1 ml; 0.02% (w/v) biotin solution 1 ml; 0.01% (w/v) thiamin solution 2 ml; yeast extract 2 g; vitamin assay casamino acid 7 g; and agar 15 g] containing kanamycin of final concentration 50 µg/mL and 4% glucose, and it was incubated at 33° C. for 15 hours in a dark place.

One platinum loop of the strain CAT92 grown on the above-described plate was inoculated in a test tube containing 10 ml of A-liquid medium [obtained by dissolving the following in 1 liter of distilled water: $(NH_2)_2CO$ 2 g; $(NH_4)_2SO_4$ 7 g; $KH_2PO_4$ 0.5 g; $K_2HPO_4$ 0.5 g; $MgSO_4.7H_2O$ 0.5 g; 0.06% (w/v) $FeSO_4.7H_2O$+0.042% (w/v) $MnSO_4.2H_2O$ 1 ml; 0.02% (w/v) biotin solution 1 ml; 0.01% (w/v) thiamin solution 2 ml; yeast extract 2 g; and vitamin assay casamino acid 7 g] containing kanamycin of final concentration 50 µg/mL and 2% glucose, and aerobic shaking culture was carried out at 33° C. for 7 to 15 hours.

Each strain grown under the above-described conditions was suspended in 10 ml of A-liquid medium containing kanamycin of final concentration 50 µg/mL and 4% glucose so that the initial bacterial cell concentration $OD_{610}$=0.5. 200 mg of $CaCO_3$ was added thereto and aerobic shaking culture was carried out at 33° C. for 48 hours. The culture solution obtained after 48 hours was centrifuged (4° C., 15,000×g, 5 minutes), whereby supernatant of culture was obtained. The concentration of metabolite in the supernatant of culture was analyzed by using a high-performance liquid chromatography system (Prominence HPLC (manufactured by Shimadzu Corporation), COSMOSIL Packed column 5C18-AR-II, separation using 10% methanol and 0.1% phosphoric acid for the mobile phase). Consequently, this strain produced 18.4 mM of catechol after 24 hours.

Example 41

Catechol Production Test (in Test Tube, 10 mL Scale) (Influence on Catechol Production by Genes From Various Organisms that Encode Enzymes Having Decarboxylation Activity with Respect to Protocatechuic Acid Derived)

In order to examine effects of the introduction of a gene that encodes an enzyme having a decarboxylation activity with respect to protocatechuic acid in the production of catechol by a *Corynebacterium glutamicum* transformant, a strain LHglc1367 in which a gene encoding a catechol degrading enzyme was disrupted was constructed on the basis of *Corynebacterium glutamicum* strain PCA3 [WO2017/169399], which produces protocatechuic acid (Table 5). Plasmids in which respective genes were incorporated were introduced in these strains, respectively, whereby decarboxylase-introduced strains CAT01 to CAT47 were obtained (Table 6). Respective catechol productivities were compared. Each strain was applied to the above-described A-agar plate containing kanamycin of final concentration 50 μg/mL and 4% glucose, and it was incubated at 33° C. for 15 hours in a dark place.

One platinum loop of each strain grown on the above-described plate was inoculated in a test tube containing 10 ml of the A-liquid medium containing kanamycin of final concentration 50 μg/mL and 2% glucose, and aerobic shaking culture was carried out at 33° C. for 7 to 15 hours.

Each strain grown under the above-described conditions was inoculated in 10 ml of A-liquid medium containing kanamycin of final concentration 50 μg/mL and 4% glucose so that the initial bacterial cell concentration $OD_{610}$=0.5. 200 mg of $CaCO_3$ was added thereto and aerobic shaking culture was carried out at 33° C. for 24 hours. The culture solution obtained after 24 hours was centrifuged (4° C., 15000×g, 5 minutes), and the supernatant of culture obtained was subjected to quantitative analysis of catechol, using the above-mentioned high-performance liquid chromatography system. The results are shown in Table 7.

Incidentally, the "amino acid sequence identity" shown in Table 7 indicates results of comparison between amino acid sequences encoded by the ubiD gene of *Lactobacillus rhamnosus*, and amino acid sequences encoded by other ubiD genes.

TABLE 7

| Strain | Introduced Decarboxylase | | Catechol Production Concentration (mM) | Amino Acid Sequence Identity (%) | |
|---|---|---|---|---|---|
| | Species | Gene | | vs. *L. rhamnosus* | vs. *B. megaterium* |
| CAT 21 | *Lactobacillus rhamnosus* | ubiDX | 44.3 | 100 | |
| CAT 41 | *Lactobacillus pentosus* | ubiXH + ubiD | 33.6 | 85 | — |
| CAT 24 | *Lactobacillus plantarum* | ubiXH + ubiD | 33.2 | 85 | — |
| CAT 42 | *Lactobacillus pobuzihii* | ubiDX | 29.4 | 82 | — |
| CAT 45 | *Lactobacillus composti* | ubiDX | 26.3 | 80 | — |
| CAT 06 | *Bacillus megaterium* | ubiXDH | 29.1 | — | 100 |
| CAT 05 | *Bacillus licheniformis* | ubiXDH | 27.1 | — | 81 |
| CAT 39 | *Bacillus atrophaeus* | ubiXDH | 23.5 | — | 81 |
| CAT 02 | *Bacillus subtilis* subsp. *subtilis* | ubiXDH | 21.8 | — | 82 |
| CAT 38 | *Bacillus subtilis* subsp. *spizizenii* | ubiXDH | 22.4 | — | 82 |
| CAT 37 | *Enterobacter aerogenes* | ubiXDH | 25.4 | — | — |
| CAT 01 | *Enterobacter cloacae* | ubiXDH | 25.4 | — | — |
| CAT 32 | *Enterobacter sakazakii* | ubiXDH | 24.9 | — | — |
| CAT 40 | *Enterobacter hormaechei* | ubiXDH | 21.4 | — | — |
| CAT 31 | *Escherichia coli* W | ubiXDH | 21.9 | — | — |
| CAT 36 | *Escherichia fergusonii* | ubiXDH | 21.9 | — | — |
| CAT 35 | *Paenibacillus polymyxa* | ubiXDH | 26.4 | — | — |
| CAT 34 | *Citrobacter koseri* | ubiXDH | 24.5 | — | — |
| CAT 33 | *Pantoea ananatis* | ubiXDH | 21.2 | — | — |
| CAT 158 | Control | — | 0 | — | — |

The results shown in Table 7 indicate that the introduction of the ubiDX gene of *Lactobacillus rhamnosus* or an ortholog of the same causes the amount of produced catechol to increase. It is indicated that the amount of produced catechol was particularly increased in the case where the strain in which the gene ubiDX of *Lactobacillus rhamnosus* or the gene having high homology with the gene ubiDX is introduced is used (for example, the strain CAT21, the strain CAT41, the strain CAT24).

Example 51

Catechol Production Test (in Jar Fermenter, 400 mL Scale) (Study on Optimal pH for Production)

By using strain CAT21 (see Tables 5 to 7), experiments of producing catechol in an aerobic batch reaction using a jar fermenter were carried out by the method described below.

The strain CAT21 was inoculated in 10 ml of the A-liquid medium containing kanamycin of final concentration 50

µg/mL and 2% glucose, and thereafter, aerobic shaking culture was carried out at 33° C. for 18 hours.

The strain CAT21 was inoculated in 100 ml of the A-liquid medium containing kanamycin of final concentration 50 µg/mL and 2% glucose, and thereafter, aerobic shaking culture was carried out at 33° C. for 12 hours.

Bacterial cells grown under the above-described conditions were collected by centrifugation (4° C., 3000×g, 10 minutes), and the bacterial cells thus obtained were suspended in 400 ml of a culture solution [obtained by dissolving the following in 1 liter of distilled water: $(NH_4)_2SO_4$ 7 g; $KH_2PO_4$ 0.5 g; $K_2HPO_4$ 0.5 g; $MgSO_4.7H_2O$ 0.5 g; 0.06% (w/v) $FeSO_4.7H_2O$+0.042% (w/v) $MnSO_4.2H_2O$ 1 ml; 0.02% (w/v) biotin solution 25 µl; 0.01% (w/v) thiamine solution 2 ml; yeast extract 2 g; and vitamin assay casamino acid 7 g] containing kanamycin of final concentration 50 µg/mL, 8% glucose, and 3 g/L of an antifoam agent (AD-EKANOL L126, manufactured by Adeka Corporation) in a 1000-ml jar fermenter culture vessel so that $OD_{610}$=0.2. Each of these was subjected to 24-hour aerated agitated culture in a 1000-ml jar fermenter under the conditions of 33° C., pH control by addition of 5.0 N aqueous ammonia, aeration amount of 0.4 L/min (air, 1 vvm), and dissolved oxygen concentration (DO) of 10% (assuming that the saturated dissolved oxygen concentration under atmospheric pressure is 100%). The concentration of metabolite in the supernatant of culture was analyzed by using the high-performance liquid chromatography system described above. The results are shown in Table 8.

TABLE 8

Comparison of Amounts of Catechol Produced in Jar Fermenter with Varied pH

| pH | Catechol Production Concentration (mM) |
| --- | --- |
| 6.0 | 39 |
| 6.5 | 51 |
| 7.0 | 60 |
| 7.5 | 50 |
| 8.0 | 0 |

The strain CAT21, in a case of being cultured with pH 7.0 being maintained, had produced 60 mM of catechol when 24 hours passed after the start of culturing, and exhibited the highest concentration, among the examined cases of various values of pH. In addition, in a case where it was cultured with pH 8.0 being maintained, the concentration of produced catechol was 0 mM at the point in time when 24 hours passed. These results indicate that in a case where catechol is produced with use of this strain, pH set in the vicinity of 7.0 leads to the highest productivity.

Example 6

Catechol Production Test (in Jar Fermenter, 400 mL Scale) (Growth-Independent Production Test)

By using the strain CAT21 (see Tables 5 to 7), experiments of producing catechol in an aerobic batch reaction using a jar fermenter were carried out by the method described below.

The strain CAT21 was inoculated in 10 ml of the A-liquid medium containing kanamycin of final concentration 50 µg/mL and 2% glucose, and thereafter, aerobic shaking culture was carried out at 33° C. for 18 hours.

The strain CAT21 was inoculated in 100 ml of the A-liquid medium containing kanamycin of final concentration 50 µg/mL and 2% glucose, and thereafter, aerobic shaking culture was carried out at 33° C. for 12 hours.

Bacterial cells grown under the above-described conditions were collected by centrifugation (4° C., 3000×g, 10 minutes), and the bacterial cells thus obtained were suspended in 400 ml of a culture solution [obtained by dissolving the following in 1 liter of distilled water: $(NH_4)_2SO_4$ 7 g; $KH_2PO_4$ 0.5 g; $K_2HPO_4$ 0.5 g; $MgSO_4.7H_2O$ 0.5 g; 0.06% (w/v) $FeSO_4.7H_2O$+0.042% (w/v) $MnSO_4.2H_2O$ 1 ml; 0.02% (w/v) biotin solution 25 µl; 0.01% (w/v) thiamine solution 2 ml; yeast extract 2 g; and vitamin assay casamino acid 7 g] containing kanamycin of final concentration 50 µg/mL, 8% glucose, and 3 g/L of an antifoam agent (AD-EKANOL L126) in a 1000-ml jar fermenter culture vessel so that $OD_{610}$=0.2. Each of these was subjected to 18-hour aerated agitated culture in the 1000-ml jar fermenter under the conditions of 33° C., pH 7.0 (controlled by addition of 5.0 N aqueous ammonia), aeration amount of 0.4 L/min (air, 1 vvm), and dissolved oxygen concentration (DO) of 5% (assuming that the saturated dissolved oxygen concentration under atmospheric pressure is 100%).

Bacterial cells of the strain grown under the above-described conditions were collected by centrifugation (4° C., 5000×g, 10 minutes), and the bacterial cells thus obtained were washed with 0.9% sodium chloride aqueous solution once. Thereafter, the bacterial cells were suspended in 250 ml of a reaction solution [obtained by dissolving the following in 1 liter of distilled water: $(NH_4)_2SO_4$ 7 g; $KH_2PO_4$ 0.5 g; $K_2HPO_4$ 0.5 g; $MgSO_4.7H_2O$ 0.5 g; 0.06% (w/v) $Fe_2SO_4.7H_2O$+0.042% (w/v) $MnSO_4.2H_2O$ 1 ml; and 0.01% (w/v) thiamine solution 2 ml] containing 10% glucose so that 100 g of wet bacterial cells were contained per liter (5% of the medium volume in terms of weight of wet bacterial cells), and a catechol producing reaction was caused under the conditions of 33° C., pH 7.0 (controlled by adding 5.0 N aqueous ammonia), aeration amount of 0.25 L/min (air, 1 vvm), DO 5%, by using a 1000-ml jar fermenter. The concentration of metabolite in the supernatant of culture was analyzed by using the high-performance liquid chromatography system described above. The results are shown in FIG. 1.

As illustrated in FIG. 1, the strain CAT21 had produced 66 mM (7.25 g/l) of catechol when 27.5 hours had passed after the start of the catechol producing reaction. The results indicate that this strain has a very high catechol productivity in a reaction process without bacterial cell growth using an inorganic salt minimal medium. The catechol productivity of this strain significantly exceeded the productivity of *Escherichia coli* recombinant strain, 38 mM (4.2 g/L) in 36 hours (Non-Patent Document 3) and 41 mM (4.5 g/L) in 84 hours (Non-patent Document 2), which is the highest productivity among the productivities by the processes of fermentation from saccharides that have been reported so far.

Example 7

Catechol Production Test (in Jar Fermenter) (Utilization of Resin Adsorption)

By using the strain CAT21 (see Tables 5 to 7), experiments of producing catechol performed in an aerobic batch reaction using a jar fermenter, with use of a resin adsorption in combination, were carried out by the method described below.

The strain CAT21 was inoculated in 10 ml of the A-liquid medium containing kanamycin of final concentration 50

μg/mL and 2% glucose, and thereafter, aerobic shaking culture was carried out at 33° C. for 18 hours.

The strain CAT21 was inoculated in 100 ml of the A-liquid medium containing kanamycin of final concentration 50 μg/mL and 2% glucose, and thereafter, aerobic shaking culture was carried out at 33° C. for 12 hours.

Bacterial cells grown under the above-described conditions were collected by centrifugation (4° C., 3000×g 10 minutes), and the bacterial cells thus obtained were suspended in 400 ml of a culture solution [obtained by dissolving the following in 1 liter of distilled water: $(NH_4)_2SO_4$ 7 g; $KH_2PO_4$ 0.5 g; $K_2HPO_4$ 0.5 g; $MgSO_4.7H_2O$ 0.5 g; 0.06% (w/v) $FeSO_4.7H_2O$+0.042% (w/v) $MnSO_4.2H_2O$ 1 ml; 0.02% (w/v) biotin solution 25 μl; 0.01% (w/v) thiamine solution 2 ml; yeast extract 2 g; and vitamin assay casamino acid 7 g] containing kanamycin of final concentration 50 μg/mL, 8% glucose, and 3 g/L of an antifoam agent (ADEKANOL L126) in a 1000-ml jar fermenter culture vessel so that $OD_{610}$=0.2. Each of these was subjected to 18-hour aerated agitated culture in the 1000-ml jar fermenter under the conditions of 33° C., pH 7.0 (controlled by addition of 5.0 N aqueous ammonia), aeration amount of 0.4 L/min (air, 1 vvm), and dissolved oxygen concentration (DO) of 5% (assuming that the saturated dissolved oxygen concentration under atmospheric pressure is 100%).

Bacterial cells of the strain grown under the above-described conditions were collected by centrifugation (4° C., 5000×g, 10 minutes), and the bacterial cells thus obtained were washed with 0.9% sodium chloride aqueous solution once. Thereafter, the bacterial cells were suspended in 300 ml of a reaction solution [obtained by dissolving the following in 1 liter of distilled water: $(NH_4)_2SO_4$ 7 g; $KH_2PO_4$ 0.5 g; $K_2HPO_4$ 0.5 g; $MgSO_4.7H_2O$ 0.5 g; 0.06% (w/v) $Fe_2SO_4.7H_2O$+0.042% (w/v) $MnSO_4.2H_2O$ 1 ml; and 0.01% (w/v) thiamine solution 2 ml] containing 10% glucose so that 100 g of wet bacterial cells were contained per liter (5% of the medium volume in terms of weight of wet bacterial cells), and a catechol producing reaction was caused under the conditions of 33° C., pH 7.0 (controlled by adding 5.0 N aqueous ammonia), aeration amount of 0.3 L/min (air, 1 vvm), DO 5%, by using a 1000-ml jar fermenter. At this time, a flow passage filled with the reaction solution from the jar fermenter in advance, and a peristaltic pump, were connected, so that circulation of the culture solution was started simultaneously. A cross flow filtration apparatus (Microza Pencil module) and another peristaltic pump were arranged in the middle of the flow passage, so that filtrate that does not contain bacterial cells was discharged. This filtrate was passed through a column packed with 60 g of an adsorption resin (SP850), and flow-through liquid was returned to the jar fermenter. After 48 hours, the experiment was ended; all the reaction solution contained in the flow passage was returned to the jar fermenter, and the volume thereof was measured. The concentration of metabolite in the supernatant of culture was analyzed by using the high-performance liquid chromatography system described above. The metabolite adsorbed to the resin was extracted by causing water, then, 100% ethanol to pass therethrough, and the aqueous extract, as it was, and the ethanol extract, dried and solidified by an evaporator and dissolved in water of the same volume, were analyzed with the above-described high-performance liquid chromatography system. The results are shown in Table 9.

TABLE 9

Amount of Catechol Contained in Culture Solution and Resin After End of Reaction

| Analyzed Sample | Volume (mb) | Concentration (mM) | Amount of Catechol (mmole) |
| --- | --- | --- | --- |
| In Culture Solution | 475 | 40.5 | 19.2 |
| Resin 1 | 100 | 42.4 | 4.2 |
| Resin 2 | 40 | 915.6 | 36.6 |
| Resin 3 | 50 | 81.1 | 4.1 |
| Resin 4 | 50 | 0.9 | 0.0 |
| Total | | | 64.2 |

The total mass of catechol products divided by the volume of the reaction solution was assumed to be the catechol production concentration. Consequently, this strain CAT21 produced 135 mM (14.9 g/L) of catechol in 48 hours. The yield with respect to consumed glucose in that case was 18% (molar ratio).

As an exemplary case of the catechol production by the process of fermentation from saccharides wherein an adsorption resin was used in combination, a case where 77 mM (8.5 g/L) of catechol was produced with use of a *Escherichia coli* recombinant strain in 36 hours, resulting in the yield of 7%, was reported (Non-Patent Document 3); however, the catechol productivity of the strain CAT21 significantly exceeded the above-described results in terms of concentration and yield.

Reference Example 1

Verification that Coryneform Bacterium Exhibits Higher Catechol Resistance, as Compared with Other Microorganisms Coryneform bacteria (*Corynebacterium glutamicum*), colon bacteria (*Escherichia coli*), yeast (*Saccharomyces cerevisiae*), Pseudomonas (*Pseudomonas putida*), and Rhodococcus (*Rhodococcus erythropolis*) were subjected to cross-streak assay on agar plates, so that their resistances against catechol were compared.

The *Corynebacterium glutamicum* strain R, and the strain ATCC 13032, were applied to the above-described A-agar plates containing 4% glucose, and were incubated at 33° C. for 15 hours in a dark place. One platinum loop of *Corynebacterium glutamicum* grown on the plate described above was inoculated in a test tube having therein 10 ml of the A-liquid medium containing 2% glucose, and aerobic shaking culture was carried out at 33° C. for 13 hours.

The *Escherichia coli* strain K-12 MG1655 was applied to a LB-agar plate [containing 1% polypeptone, 0.5% yeast extract, 0.5% sodium chloride, and 1.5% agar], and was incubated at 37° C. for 15 hours in a dark place. *Escherichia coli* grown on the plate described above was inoculated in an LB-liquid medium [containing 1% polypeptone, 0.5% yeast extract, and 0.5% sodium chloride], and aerobic shaking culture was carried out at 37° C. for 13 hours.

The *Pseudomonas putida* strain ATCC 700801 was applied to the above-described LB-agar plate, and was incubated at 30° C. for 15 hours in a dark place. *Pseudomonas putida* grown on the plate described above was inoculated in the LB-liquid medium, and aerobic shaking culture was carried out at 30° C. for 13 hours.

Further, the *Saccharomyces cerevisiae* strain NBRC2376 was applied to a YEPD agar plate [2% polypeptone, 1% yeast extract, 2% glucose, and 1.5% agar], and was incubated at 30° C. for 20 hours in a dark place. *Saccharomyces cerevisiae* grown on the plate described above was inoculated in a YEPD liquid medium [2% polypeptone, 1% yeast extract, and 2% glucose], and aerobic shaking culture was carried out at 30° C. for 13 hours.

The *Rhodococcus erythropolis* strain ATCC 27854 was applied to the LB-agar plate, and was incubated at 30° C. for 15 hours in a dark place. *Rhodococcus erythropolis* grown on the plate described above was inoculated in the LB-liquid medium, and aerobic shaking culture was carried out at 30° C. for 13 hours.

Each strain preliminary cultured as described above was uniformly applied in a line form onto the above-described A-agar plates containing 4% glucose, and filter paper impregnated with 25% catechol was placed on each plate at the center thereof so as to intersect with the lines. After being incubated at 30° C. or 26° C. for 24 hours in a dark place, growth inhibition ranges of the strains from the filter paper were compared so that resistances thereof were compared. The results are shown in FIG. 2.

Figure 2:
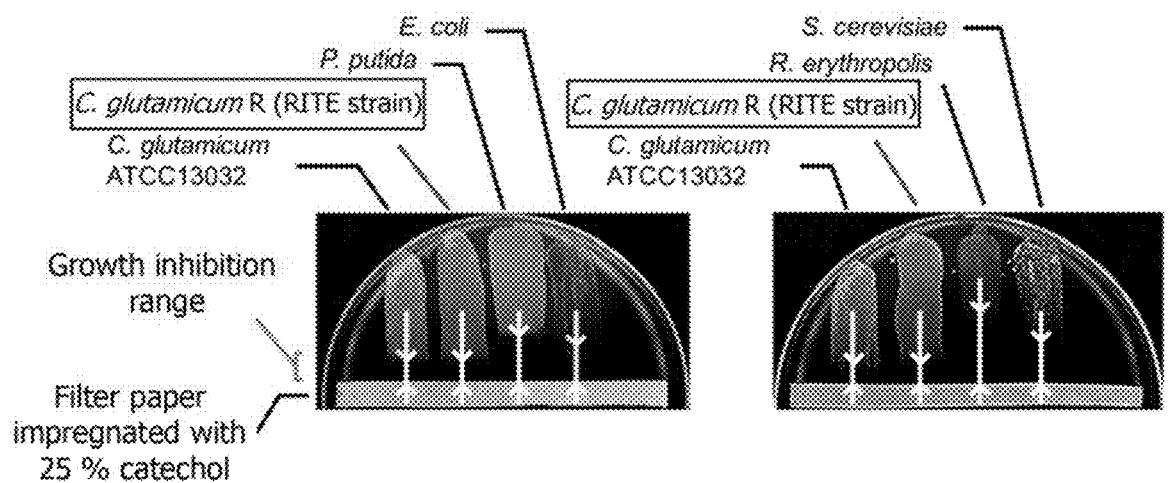
FIG. 2 shows an exemplary experiment that indicates high resistance of a coryneform bacterium against catechol.

As illustrated in FIG. 2, the results indicate that the coryneform bacteria have narrower growth inhibition ranges than any of the other bacteria, and have relatively high resistances. In addition, no clear difference was seen between the results of the coryneform bacterium strain R and those of the strain ATCC 13032.

INDUSTRIAL APPLICABILITY

The present disclosure is useful for, for example, producing catechol.

[Sequence Listing]

The invention claimed is:

1. A transformant of a *Corynebacterium* obtained by introducing,
   into the *Corynebacterium*, at least one gene selected from the group consisting of:
   (1) a decarboxylase gene ubiD of *Lactobacillus rhamnosus*; and
   (2) at least one ortholog of the decarboxylase gene ubiD of *Lactobacillus rhamnosus*,
   wherein one or more substitutions, deletions and/or insertions are introduced into a catechol 1,2-dioxygenase gene catA, and a protocatechuic acid dehydrogenase gene pcaHG in the *Corynebacterium*, thereby degrading or losing functions of enzymes encoded by the catechol 1,2-dioxygenase gene catA and the protocatechuic acid dehydrogenase gene pcaHG,
   wherein the *Corynebacterium* is selected from the group consisting of: *Corynebacterium glutamicum*, *Corynebacterium efficiens*, *Corynebacterium ammoniagenes*, and *Corynebacterium halotolerance*,
   wherein the ortholog of the decarboxylase gene ubiD of *Lactobacillus rhamnosus* is selected from the group consisting of: an ubiD gene of *Lactobacillus pentosus*, an ubiD gene of *Lactobacillus plantarum*, an ubiD gene of *Lactobacillus pobuzihii*, an ubiD gene of *Lactobacillus composti*, an ubiD gene of *Bacillus megaterium*, an ubiD gene of *Bacillus licheniformis*, an ubiD gene of *Bacillus atrophaeus*, an ubiD gene of *Bacillus subtilis* subsp. *subtilis*, an ubiD gene of *Bacillus subtilis* subsp. *Spizizenii*, an ubiD gene of *Enterobacter aerogenes*, an ubiD gene of *Enterobacter cloacae*, an ubiD gene of *Enterobacter sakazakii*, an ubiD gene of *Enterobacter hormaechei*, an ubiD gene of *Escherichia coli* W, the ubiD gene of *Escherichia fergusonii*, an ubiD gene of *Paenibacillus polymyxa*, the ubiD gene of *Citrobacter koseri*, and an ubiD gene of *Pantoea ananatis*, and wherein the transformant has a catechol producing ability.

2. The transformant of claim 1,
wherein the *Corynebacterium* is *Corynebacterium glutamicum* R (FERM P-18976), ATCC13032, or ATCC13869.

3. A transformant of *Corynebacterium glutamicum* CAT21 deposited under Accession Number: NITE BP-02689.

4. A method for producing catechol comprising:
reacting the transformant of claim 1 in a reaction solution under reducing conditions; and
collecting catechol in a reaction solution.

5. The method of claim 4,
wherein the reaction solution comprises at least one saccharide selected from the group consisting of glucose, fructose, cellobiose, xylobiose, sucrose, lactose, maltose, dextrin, xylose, arabinose, galactose, mannose, and soluble starch.

6. The transformant of claim 1, wherein the *Corynebacterium* is *Corynebacterium glutamicum*.

* * * * *

SEQUENCE LISTING

<160> NUMBER OF SEQ ID NOS: 73

<210> SEQ ID NO 1
<211> LENGTH: 2058
<212> TYPE: DNA
<213> ORGANISM: Lactobacillus rhamnosus

<400> SEQUENCE: 1

```
atgacagcat caccttggga cttaagaaaa gtattggatg aactaaaaca ggatccgcag      60
caatatcatg aaacagaggt gcaagtcgat cccgatgcag agcttgctgg cgtttatcgt     120
tacatcggtg ccggtgggac ggtcgaacgt ccgacacagg aaggtccggc aatgatgttt     180
aacaacgttg tcggcttccc aacgacaagg gttttgatcg gtttaatggc cagtcgcaag     240
cgggttggca agatgtttca ccaagactat cacacacttg gtcgattctt gaacaaagcg     300
gttttaaatc ctattcaacc cgttacagtc gaagaatcag cagcgcctgc gcatgaagtc     360
gttgccaagg ctagtgaccc ggactttgac attagaaaac tcgttgcagc accaaccaat     420
acgccacaag atgccggccc atacatcaca tgcggcgtag ttttgggttc caatatggcc     480
aaaacaatga ctgatgtgac gattcatcgc atggttttgg aagataagga tacgcttggt     540
atttatatca tgcccggtgg tcgccacatt ggtcattttg ctgaagaata tgaaaaagcc     600
aataagccga tgccggtgac catcaacatt ggcttggatc cggccattac cattggtgcc     660
acttttgaac cgcctaccac gccgcttggc tacgatgaac taggagttgc cggagccatt     720
cgccaagaac ccgtgcaact ggttcaggct gtgaccgtca atgaaaaagc cattgcgcgt     780
tcagaattta cactggaagg ctatatcatg cctaacacgc gtatccaaga agatatcaat     840
acccataccg gcaaagccat gccagagttt cccggctatg acggtgatgc caatccggct     900
ttgcaagtga ttaaagtgac ggctgtaacc catcggcgcg atcatcccat tatgcaaagt     960
gtcatcggac ctagtgaaga acatgtctcc atggccggca ttccaaccga agccagcatt    1020
ttacaacttg ttgatcgtgc catccccggc aaggtcaaga atgtgtacaa tcccccagct    1080
ggtggcggca aactcatgac catcatgcaa attcacaaag ataatccagc tgatgaaggg    1140
attcaacgtc aagctgcatt actcgctttt tcggcattca aagaactaaa aactgtttgg    1200
ctggtcgatg atgatgtcga tattttgac atgaatgatg tcgtctggac aatgaacacg    1260
cgttttcaag gtgatcagga catcatggta ttacctggca tgcgcaacca tccgcttgat    1320
ccgtcagaac gaccgcaata tgatcccaag tctattcggg tacgcggaat gagttcgaag    1380
acggtcattg atggtaccgt accatttgat atgcgcgatc aattcaaacg agcagccttt    1440
```

-continued

| | | |
|---|---|---|
| aaaaaagttt ccgactggca aaaatatttg aaataggtga ttgaattgaa acgtattatc | 1500 |
| gtagggatta ccggggcatc cggaactatt tacgctgtta acctgctcca gcatttacat | 1560 |
| cgcctgcctg atgtcgaagt tcatttggtg atgagtgctt gggcaaagca aaacctgtca | 1620 |
| cttgagaccg acatgaaaca aagcgaactc gaagctttgg cggattatgt ttatcctgtt | 1680 |
| caaaaccaag gggcaaccat tgcaagcggc agttttttaa ccgatgcaat ggtcattgtt | 1740 |
| ccggcaagca tgaaaaccat tgcgggcatt gcgatgggct ttgatgataa tctcattgga | 1800 |
| cgagcagccg atgtcacgat taaagaacag cggcaattga ttattgtgcc gcgggaaaca | 1860 |
| ccgcttagtc caattcatct ggataacctc gctaaactag cccacattgg cgttcaaatc | 1920 |
| attccgccta ttccagcttt ctatcagcat ccccaaacca tccaggattt aattgagcat | 1980 |
| cacaccatga aactattaga cgccttgcat attaaaaccg aaaccgctag tcgctggaat | 2040 |
| ggagcgtcgt taagatga | 2058 |

<210> SEQ ID NO 2
<211> LENGTH: 977
<212> TYPE: DNA
<213> ORGANISM: Lactobacillus pentosus

<400> SEQUENCE: 2

| | | |
|---|---|---|
| atgaagcgaa ttgttgtcgg aattacaggg gcgtcaggaa cgatttatgc cgttgattta | 60 |
| ttagagaagt tacaccaact ccctgatgtt gaagtgcatc tagttatgag tgcttgggcg | 120 |
| aagaagaact tggagctcga gacggattac tcacttgcac aattgacggc attggcggat | 180 |
| gcgacttacc gtgctaacga ccaggggggcg gcaatcgcga gcggttcatt tttaaatgac | 240 |
| ggtatggtga tcgttccagc cagcatgaag accgttgccg gaattgctta cggctttggc | 300 |
| gataatctga tttcacgtgc agccgatgtg acgatcaagg agcaacgtaa actcgtcatt | 360 |
| gttccacgtg aaacacccct tgagtgtgatt catttggaga atctgacgaa attagccaag | 420 |
| ttgggtgcac aaatcattcc accgattccg gccttttata accatccgac cacgattcaa | 480 |
| gacttggtta accatcagac gatgaaaatc ttagatgcct tccatattca taatgaaacg | 540 |
| gatcgccgtt gggaaggaga ttagccatgc ccacttttac gactgaacaa gcaggttatc | 600 |
| agatgcaagc caccgttcag gttatcggat atgacttatt gattgtcgtt acgggcggca | 660 |
| ccaatccgca tattggtgat gtgaccacca ttacagcaac gatgccggcc caaaccgtca | 720 |
| aatttcctag tcacgatggc cgttttcaca aggataactt catttcggat cgaatggcga | 780 |
| agcgcctgca gtcgtcgttg ccgggaagtt gcacgattac tgctggaatt catgtcaacc | 840 |
| agattactaa ggcacagatt gcggccgctg caccaatgac ggatgattta agccagcaaa | 900 |
| ttattacttg gctacaagca cacccccattc aggctgctcg gccggaatac tacggggatg | 960 |
| atgagcagcc gaagtag | 977 |

<210> SEQ ID NO 3
<211> LENGTH: 1473
<212> TYPE: DNA
<213> ORGANISM: Lactobacillus pentosus

<400> SEQUENCE: 3

| | | |
|---|---|---|
| atggcagaac aaccatggga tttacgccgg gtacttgatg agatcaaaga tgatcccaag | 60 |
| aactatcatg aaaccgacgt tgaagtagat ccaaatgcgg aactttctgg tgtttatcgg | 120 |
| tatattggtg ctggtgggac cgttgaacgg ccaaacacaag aaggtccagc aatgatgttc | 180 |
| aacaacgtga agggttttcc tgacacgcgt gtcttgactg gtttaatggc tagccgtcgt | 240 |

```
cggggttggta agatgttcca tcatgattac caaacgttag gtcaatatct taacgatgca      300
gtttcaaatc cagttgcacc ggaaacggtc gctgaaaagg atgcaccggc tcacgaagtc      360
atttacaagt caactgatga aggctttgat attcggaagt tagttgcagc gccaactaat      420
acgccacaag atgctggtcc atatatcacg gtcggtgttg tcttcggttc aagcatggac      480
aagtccaaga gtgacgttac gattcaccgg atggttcttg aagacaagga caagctcgga      540
atctacatca tgcctggtgg ccgtcatatc ggtgcctttg ccgaagaata tgaaaaggcc      600
aataaaccaa tgccaatcac gatcaacatt ggtttggatc ctgccattac cattggtgcc      660
acctttgaac cacctaccac cccatttggt tacaacgaat taggggttgc tggtgccatt      720
cggaatcaag ccgttcaatt agtcgatggg gttaccgttg atgaaaaggc gattgcacgt      780
tctgaataca cgttggaagg ctacatcatg cctaacgaac ggattcaaga agacatcaac      840
acccatacgg gtaaagcgat gcctgaattc ccaggttatg atggtgatgc taacccagcc      900
ttacaagtca tcaaggtgac ggcggtaacg catcgggaaa atgccatcat gcaaagtgtt      960
atcggaccat ccgaagaaca tgtcagcatg gctggtattc caaccgaagc aagtatctta     1020
cagttagtta accgcgccat tcctggcaaa gtgactaacg tttacaatcc gccggctggt     1080
ggtggtaagt tgatgaccat catgcagatt cataaggata tgaagcgga tgaagggatt     1140 caacggcaag cagccttatt ggcgttctca gcgttcaagg aattgaagac ggtcatttta     1200
gttgatgaag acgttgatat ttttgatatg aacgatgtga tttggaccat gaatacccgt     1260
ttccaagctg accaagactt gatggtctta tctggcatgc ggaaccatcc attggatcca     1320
tcagaacggc cacaatacga tccaaaatcg attcgtttcc gtgggatgag ttcgaagttg     1380
gttatcgatg gcactgtacc attcgatatg aaagaccaat ttgaacgggc tcaattcatg     1440
aaggtcgatg actgggaaaa gtatttgaaa taa                                  1473

<210> SEQ ID NO 4
<211> LENGTH: 977
<212> TYPE: DNA
<213> ORGANISM: Lactobacillus plantarum

<400> SEQUENCE: 4
atgaaacgaa ttgttgtggg aatcacggga gcgtccggta cgatttacgc ggtcgactta       60
ttagaaaagt tacatcagcg gccagatgtt gaagttcacc tggtaatgag tgcgtgggct      120
aaaaaaaact tggagttaga gactgattac tcgctcgcgc agttgacggc gctcgcggat      180
gctacttatc gggctaatga ccaaggcgca gcgattgcca gtggtcgtt tttgaatgac      240 ggaatggtca ttgtcccagc tagtatgaag acggtagcgg ggattgcgta cggcttcggt      300
gataatttaa tatcgcgggc tgctgatgtc acgattaaag aacaacgtaa acttgtgatt      360
gttccacgtg aaacaccgtt aagcgtgatt catttagaaa atctaacaaa gttggcaaaa      420
ctcggtgccc aaattattcc accgattccc gcttttttata atcatccaca gtccattcag      480
gatctggtca atcatcaaac aatgaaaatt ttggatgcgt ttcatattca taatgaaact      540
gatcgccgtt gggaggggga ttaagtatgg caacttttac gactgagcag gccgggtatc      600
aaatgcaagc aacactccaa gtgattggat atgacttgtt gatcgtcgtt accgtgggga      660
ccaatcccca tattggtgac gtgaccacac taactgccag cacggttccc gaaacggtta      720
agtttcccag cctatgatggt cgcttccata agataactt tatttcggaa cgaatggcca      780
agcggattca gcgttatcta gctggaagct gtacaattac tgcgggaatt catgtcaacc      840
```

```
aaattactaa agcacaaata gcagctgcgg caccaatgac ggatgacctc agccgccaga      900
ttattagctg gttacaggcc catcccgtcc aggctgaaaa gccggaatat tatggacaag      960
atgagcaacc gcggtag                                                     977

<210> SEQ ID NO 5
<211> LENGTH: 1473
<212> TYPE: DNA
<213> ORGANISM: Lactobacillus plantarum

<400> SEQUENCE: 5
atggcagaac aaccatggga tttgcgtcgc gtgcttgatg agatcaagga tgatccaaag       60
aactatcatg aaactgacgt cgaagttgat ccaaatgcgg aactttctgg tgtttatcgg      120
tatatcggtg ctggtgggac cgttcaacgg ccaacgcaag agggtccagc aatgatgttt      180
aacaacgtta aggggtttcc tgatacgcgg gtcttgactg gattgatggc gagtcgccgg      240
cgcgttggta agatgttcca ccacgattat cagacgttag ggcaatactt gaacgaagca      300
gtctctaatc cagtggcgcc agaaacggtt gctgaagcgg atgcgccagc tcacgatgtt      360
gtttataaag cgacggatga aggctttgat attcggaagt tagtggcagc accaacgaat      420 acgcccaag atgctggacc atatattacg gtcggtgtgg tgtttggctc aagcatggac       480
aagtctaaga gtgatgtgac gattcaccga atggtccttg aagataagga taagttaggg      540
atttatatca tgcctggcgg tcggcacatt ggtgcgtttg cggaagagta tgagaaagct      600
aacaagccaa tgccaattac aattaatatt ggtttggatc cagccattac gattggtgca      660
actttcgaac caccgaccac gccattcggt tataacgaat taggtgttgc tggtgcgatt      720
cggaaccaag ctgttcaatt agttgacggg gtgaccgtcg atgaaaaggc gattgcgcgt      780
tctgaatata cgcttgaggg gtacattatg cctaacgaac gtattcagga agatatcaat      840
acgcatacgg gcaaggcgat gcctgaattc ccgggttatg atggtgacgc caacccagct      900
ttacaagtga ttaaggtgac ggcggtgact catcggaaga atgccatcat gcaaagcgtg      960
attggaccat ccgaagaaca tgtcagcatg gcgggaattc caactgaagc tagtatctta     1020
caattggtta accgtgccat tcctggtaaa gtgacgaatg tttataatcc gccggctggt     1080
ggtggtaagt tgatgaccat catgcagatt cacaaggata tgaagcgga tgaaggaatt      1140 caacggcaag ctgccttgct tgcgttctca gcctttaagg aattgaagac tgttatcctg     1200
gttgatgaag atgttgatat ttttgatatg aatgatgtga tttggacgat gaatacccgt     1260
ttccaagccg atcaggactt gatggtctta tcaggcatgc ggaatcatcc gttgacccca     1320
tcggaacgcc cacaatatga tccaaagtcg attcgtttcc gtgggatgag ttctaaacta     1380
gtgattgatg gcaccgtacc attcgatatg aaggaccaat ttgaacgggc ccaattcatg     1440
aaagtggctg actgggagaa gtatttgaag taa                                  1473

<210> SEQ ID NO 6
<211> LENGTH: 2043
<212> TYPE: DNA
<213> ORGANISM: Lactobacillus pobuzihii

<400> SEQUENCE: 6
atgggtgaag acaaatggga tttgcgtaaa gttttgtctg agatcaaaga tgatcccaaa       60
aactatcatg aaacagatgt cgaagttgat ccagaagctg aattagccgg tgtttatcga      120
tacattggtg ctggtgggac agttgaacgt ccaacacaag aaggacctgc gatgatgttt      180
aataatgtca aaggctttcc tagtacacgt gttttgattg gcttaatggc cagtcggaga      240
```

```
cgtgtaggaa aaatgctcca tcatgattat cagacattag gtcaattctt taatgaagca        300
gtttcgaaac cggttcctcc agttttggtt gacgaaaagg atgcacctac gcatgaagtt        360
gtgcaccatg caacagataa gaattttgat attcgtaagt tagtcgctgc tcctacaaac        420
acaccccaag atgctggtcc ttatattaca gttggtgtag ttttagggtc taacatggat        480
aagacgatgt cagatgtgac tatccatcgt atgtgcattg aaggaaaaga taagttggga        540
atttatatta tgcctggcgg aagacatatt ggggcttttg ctgaagaata cgaaaaggct        600
aataagccga tgcctgttac gatcaatatt ggacttgacc cagcagtaac gattggtaca        660
acattcgagc cgccaacaac tcctcttggt tacaatgagt taggggttgc aggttcgatt        720
cgtaaccagc ctgttgaatt ggtcaatggt gtttcagtag atgaaaaagc aattgcacgg        780
gctgaatata ctttagaagg ctatattatg cctaacgaaa gaatgcaaga agatatcaat        840
actcgtacag gtaaagcaat gcccgaattt ccaggttatg atggtgatgc taatcctgca        900
gttcaagtta taaagttac ggccgttacc catcgtaaag atccaattat gcaaagtgtg        960
atcgggccaa gtgaagaaca cgtcagcatg gcaggaattc cgactgaagc aagcatttta       1020
caattagtca ataaggctat tcctggtaag gttactaagg tttataatcc atcagcgggc       1080
ggtggcaagt tgatgactat tatgcagatt cataaagaaa acgaagcaga tgaaggtatt       1140
caacgtcaag cagctttact tgcattctct gcttttaaag aactaaagac tgtatttta       1200 gttgacgaag atgttgatat tttcgatatg aatgatgttg tttggacgat taataccagg       1260
ttccaggctg ataaagatat catggtactt tctgggatgc gtaatcatcc attggatccc       1320
tctgaacgtc ccgaatatga tccgaaatca attcgttttc gtggaatgag ttccaagtta       1380
gttgttgatg ggactgttcc attcgacatg aaagaccagt ttgaaagagc gcagtttatg       1440
aaggttccag actggaaaaa atatttggag taatcaacaa tgaaaaaaat tattattgga       1500
gtttccggag catcgggaac aatctatgca gttgatcttt tgaaaaaaac tcagcagtta       1560
tccaatgttg aaactcacct agtaatgagt aagtgggcta agcaaaatct tgcactggag       1620
acaaattatc agttaaatga aatcaactct ttggctgatt atgtatacga cgagcgagat       1680
caagctgcca aaattgctag cggttctttt ttagttgatg gtatggtcgt tgttcccgca       1740
agtatgaaaa ctatcgcagg tatagccaat ggatttgctg ataatttggt tggtcgggca       1800
gccgatgtca tacttaagga acaacgaaaa cttgtgatag ttcctcgtga atcgccttta       1860
agcgtgatcc atcttgaaaa tttaactaaa ttagctaaaa ttggggccca gatcattccc       1920
ccgattccag ccttttataa ccatccttct tctattcaag accttgtgga ccatcagacg       1980
atgaaaacct tagatgcatt gggaatcaac aatgatatat cttcacgttg ggatggcaga       2040
tga                                                                      2043
```

<210> SEQ ID NO 7
<211> LENGTH: 2055
<212> TYPE: DNA
<213> ORGANISM: Lactobacillus composti
<400> SEQUENCE: 7

```
atgtcagatt attatgattt gagacgggtc ttaaaggaat tagcagctga ggcccctaag         60
caatatcacg ccaccgatga attggtggac cctaatgcgg aattagctgg agtttaccgc        120
tacattggcg ctgggggcac ggtcaagcgg cccactcaag caggaccggc attgatgttc        180
aacaacgtca agggctttgc cggcacccgg gtcttgattg gcttattggc cagtcgcaag        240
```

```
cgggtgggtt tgctatttca tcacgattac catacgctag gccaatttct aaatgatgca    300
gtggaccatc ccctaaaccc ggtgacagtt tctgaagctg acgccccggc ccatgaagtc    360
atccacaaag tcgacgaccc tgattttgat atccgcaaac tcatcgccgc ccccaccaat    420
accgaatacg acgcagggcc ttacatcacc atgggcttag tttatgggtc taatcgggcc    480
aaaaccaaaa gtgatgtgac cattcatcgc atggtttag aggataaaga taccattggc     540
atctacatca tgcctggggg ccggcatatc ggcgcttttg ctgaagaata tgagcaagcc    600
aacgaaccca tgcccattac tgtgaacatc ggcttagatc cggccatcac gttggggggcc   660
acctttgaac cgcctacaac gcccttaggt tataacgaat tgggagttgc cggggctatt    720
cgccaagaac ccgtccagct ggtagacgct atcaccgttg ccgaaaaggc catcgcccgt    780
tctgaattca ccatcgaagg ctacatcatg ccccaccaac gcatgcaaga agacatcaac    840
accaacacgg gtaaagccat gccagaattt cctggctatg acggtgatgc taatcccgcc    900
gtgcaggtca tcaaagtaac ggcggtcacc catcgtcaag accagcccat tatgcagaca    960
gtgattggtc ccagcgaaga acatgtgaac ttagccggaa ttcccacgga agctagcatt    1020
ctagaactca ccaataaagc catccccggt aaagtcttaa atgtctacaa tcccctgct   1080
ggcggcggta aattgatgac gattctccag atccacaaaa ctaatcccgc tgatgaaggc   1140
atccagcgtc aggccgccct cttagccttt gcggcttta aagaattgaa gacagtgatt    1200
ttagtggacg aggatgtgga catttcgac atgaacgatg tgatatggac tgtcaatacc    1260
cgttttcagg ccgaccagga cattgtggtg ctgccgggga tgcgcaatca tcccctggac    1320
ccttcagagc ggcccgctta tgacccgaag tctattcgag ttcaggggat gtccagcaag    1380
ttgattttag atggcaccgt ccctggggac atgaaggctc agttcatccg agcccggttt    1440
aaagaagttc aagactggcg caagtatttg cataggaag tctgttaaac tatgaagaaa     1500
attgtcgttg ctatgaccgg cgcgtcaggc gtgatttacg gccttgattt attgcgccat    1560
ttgcaggcca ttccgtcggt tgaaacccac ctggtgctca gtccctggc taaaaagaat     1620
attcaactag aaaccgatct gaccttgcag caggtccaag atttgtccga tgtggtctac    1680
cacgacaatg accaagggc ggcgattgcc agtggttctt tcctgcacga tggcatggtg    1740
atcgtcccgg ccagcatgaa gaccgtggcc gaaatcgcct acggcttcgg ggaaaatctg   1800
attggccggg cggctgatgt gaccattaaa gaatgccgac cgctgatcat cgtacctaga   1860
gaaacgccct tgagcgtgat tcatttggaa atctcacca agctggccaa attaggagct     1920
caaatcattc cccctattcc cagttttta acccagccta agaccatcgc cgatttggtg    1980
accaaacaaa ccatgcactt attagacgct ctaaagatcc caacgacctt ggctcaacgc   2040
tggacgggag ggtaa                                                    2055
```

<210> SEQ ID NO 8
<211> LENGTH: 2517
<212> TYPE: DNA
<213> ORGANISM: Lactobacillus hokkaidonensis

<400> SEQUENCE: 8

```
atgacagaac aaccatatga tttaagaaaa gtacttgcag aaattaaaga tgaccccatg     60
caataccacg aaacaaatcg agaaatcgat ccaaatgcag atttagctgg tgtctatcga   120
tatattggtg cgggtggaac cgttaagcgt cccaccactg aagggccaac aatgatgttt   180
aataatgtta aaggatttcc aggtagtcgg gtgctgattg gattacaagc ctctcgtaaa    240
cggggttggta agatcttgca tcatgattac aaaacgttgg gtcaaatgct aaacgaggct    300
```

```
gtttcaaatc ctgtcaaacc agtagaagtt aaaagagaag atgcacctgc tcaagaagta      360
gtacacctag cgtcagattc taactttgat attcgtaaat tactagctgc gccgacgaat      420
actcctgagg acgcaggtcc atatatcaca atggggttg tgtatggtca tagcgtggat       480
ggtaagcaaa gtgatgttac aattcaccga atggttttag aagataaaga tacaatcggt     540
atgtatatca tgccaggtgg ccgccacatt ggtgcatttt taaaagacta tgagcaacaa      600
aacaagccaa tgccgatcac aattaatatt ggtttagatc ccgcagttac gattggggca      660
acctttgagc caccgacgac accactgggc tacaatgagc ttcaggtagc tggtgcattg      720
agaaatgagc cagtacaagt ggttcccgga gttgcagtaa acgcgttagg tattgcgcgc     780
tcagaatgga ttattgaggc tgaaattcaa cctaatcaaa caatgcaaga agacatcaat     840
acaaataccg gttacgcaat gcctgaattt cctggctaca atggaaccgc gaatccagcc     900
gttaatgtcg ttaaaattaa ggctgtgacg caccggaaag ataatccaat cgtccaaaca     960
actattgggc catctgaaga gcatgtttcc atggctggaa ttccaactga gcttcaattt     1020
ttaagtttag ttgatcgtgc cattccgggt aaagttttga atgtttataa cgctcccgct     1080
ggtggtggta aattaatgac catcatgcaa atccataagg ataatgaagc ggatgaagga     1140
attcaacgac aagcagcatt attagcattt tcagcgttta agaattaaa aacggtcatt       1200 ttagttgacg aagatgttga tattttgac tggaacgatg taatgtggac gatcaatacg       1260
agattccaag ctgatcgtga cattatggta ctcgagggga tgcggaatca tccgcttgac     1320
ccatcagaac tgccggaata tgatcctgct cgaatccgag tgaagggaat gagttctaaa     1380
ttagtccttg atggtaccct cccttatgat atgcgtgaca aatttaaacg gcagaatttt     1440
aaagaaattc cggattggaa gaaatatttg gattaattaa ggagggcaa atgaaaaagg      1500 ttgtcgttgg aattactggt gctagtggaa caatctacgg gattcgtta ttagaagttt      1560 tgcacgcaat gccaaatgtg gagacacacc tagtgatgag tcagtgggcc aaggaaaatt    1620
tagcagtaga agatactggt tatacggaaa ctcaagtcaa agcactggct gatttgactt    1680
attctgagca aaatatgggt gccaaaattg ctagtggcag cttatcat gatggaatgg       1740 ttattattcc agctagtatg aagactgttg catcgattgc tactggtgta ggagaaaact     1800
taattgcacg agcagccgac gtgactctaa aagaacagcg acaattgatc attgtgcctc     1860
gtgagtcgcc gtttaaccaa attcatttgg agaatatgct caaactttcc aaaatgggtg     1920
tgggtattat tccaccaatt ccggcatttt ataataatcc aaaaacggta gatgacatta     1980
tcaatcattc cgtgatgaag atcttggatc attacagat tgagaattct gttagtacac     2040
gatgggaggg attggctcat gcccgcaaag atgcccaaaa caataacga gattccgaac      2100 acttttaaag tagatgtaac aaaaagtggt tatacgatgg ttgccatttt ggaacgtcaa     2160
aatcaagatg tgctgatcca attaattgga ggcgatgtgc cgcactacgg ggttgtgatg     2220
tcgattgata atacaggcaa tactgagaca attcggttgc ctagccgccc aggacatgta     2280
catcaggaaa agattctgat tgaacaagtt gctggcgcca tcaaaccagt tttgcaaaat     2340
aatgcgatca ttgtttctgg aatgcatgtc aatgatatct ccacagaaca gatgcatgcc     2400
gctattccaa tggcgcaaaa gttgggcgca cgactagcag tttggttaaa acaaaatccg     2460
gttgatccat taccgatgag tttcgctaag aaaaacagtg tgaacaaccg cgtttag       2517

<210> SEQ ID NO 9
<211> LENGTH: 2491
<212> TYPE: DNA
```

<213> ORGANISM: Lactobacillus sakei subsp. sakei

<400> SEQUENCE: 9

| | |
|---|---|
| atgagtgaac aaccttatga tttacgtaaa gtattggctg aaatcaaaga tttaccaggc | 60 |
| caatatcatg aaacggatgt tgaaattgat cccaatgctg atttagcggg tgtctatcgt | 120 |
| tatattggtg ctggcgggac agtcatgcgg ccaacaaccg aaggcccaac aatgatgttt | 180 |
| aataatgtta aaggcttccc tggaagtcgt gttttaattg gcttgcaagc ttcacgccaa | 240 |
| cgggtcgcaa cgattttaca tcatgactac aaaacgctgg gtcaaatgtt aaacgaagcg | 300 |
| gtaaccaaac cagttgcccc cgtcgaagtg acacgcgaac aagcaccagc acaagaagtc | 360 |
| gttcatttag cgagcgatgc tgattttgat atccgcaaat tattagcagc accaaccaat | 420 |
| acggaagacg atgctggtcc atacatcaca atgggtgtcg tgtatggtca tagcgtggat | 480 |
| caccaacaaa gcgacgttac gattcaccga atggttcttg aagataaaga tacaattggg | 540 |
| atgtatatca tgcccggtgg tcgccatatc ggtgcgttct aaaagaata tgaagcaatc | 600 |
| aacgaaccaa tgccaattac cattaacatt ggtttggacc cagcgattac cattggggct | 660 |
| acttttgaac cacctacaac gccacttggt tataatgaac tccaaattgc cggtgcttta | 720 |
| agaaatgaag ccgttcaagt agtgcctggt gtcgctgttg atgccttagg gattgcccgt | 780 |
| gctgaatgga ttatcgaagc cgaaatttta ccaaaccaat caatgcaaga agatattaat | 840 |
| acgaattctg ggtatgcgat gccagaattc cctggttata cggctcagc aaatcctgcc | 900 |
| gtgaatgtga ttaaagttaa agcggtcact catcgtcaag ataatccaat tgttcaaaca | 960 |
| acaattggtc cttcagaaga acacgtttcg atggccggta ttccaactga gcatcaatt | 1020 |
| ttgagcttag tggagcgcgc tattccaggt aaagtattga acgtctataa cgcccctgct | 1080 |
| ggtggtggga aattaatgac tatcatgcaa attcataagg ataacgaagc cgatgaaggg | 1140 |
| attcaaagac aagcagcatt gctcgccttt tctgccttca agaattaaa gacggtcatc | 1200 |
| ttagtggatg aagatgttga tatcttcgat tggaacgacg tgatgtggac catcaataca | 1260 |
| cggttccaag ccgatcggga catcatggtc ttagaaggtt tacggaatca tccattagat | 1320 |
| ccatctgaat taccagaata cgatccagct cggattcgtg tgcgtgggat gagttctaag | 1380 |
| ttagtattag acgggacttt cccatatgac atgcaaaaga gtttcaagcg tgcgcaattt | 1440 |
| aaagaaatcg cagattggca aaaatattta aattaattag aagaaagggg gaataatatg | 1500 |
| cgtaaaatag tcgtcggtat ttcgggtgcc agtgggacaa tttatgggat tcgtttgcta | 1560 |
| gaggcattac accaagtgcc ggatgttgaa acacatctgg tcatgagtcg ctgggccaaa | 1620 |
| gaaaatttag ccatcgaaaa aactgggtac actgaaaagc aagtcgtggc gctagctgat | 1680 |
| tttgtccatc cagagcaaaa tatgggcgca acaattgcca gcggtagttt caaacacgat | 1740 |
| gggatggtga ttgtacccac tagcatgaaa actttagctt cgattgcaac cggtctgggc | 1800 |
| gaaaacttga ttgccagagc tgccgatgtt actttgaaag aacgacgacc attaattatt | 1860 |
| gtgccccgtg aatctccttt taatcagatt caccttgaaa atatgttgaa gttggcccaa | 1920 |
| atgggtgtgg cgattgtacc gccgattcca gcttttttata tcaaccaca acgatagat | 1980 |
| gatatcgtca atcatacggt aatgaaatta ttggatcaac tgcatatcga gccaaccctt | 2040 |
| ggttcacgtt gggaggggtt agctaatgca cgtcaaaacg ctcgctagta ccgaacaaac | 2100 |
| cgtacaattt gcggtcactg aaacggatta taacatgcac ttaaaattag agcgccaaac | 2160 |
| gtctgattta ttaattcaga ttatcggtgg cgacgtgccc cattacggcg tcatcacgac | 2220 |
| ggtcgataaa acgggtaagg cattgaccac ggcacttcct agccgccag gacatgtcca | 2280 |

-continued

| | |
|---|---|
| tcaagaaaaa gtattaattg atcaggtttt aaaaactgtt aagccactga ttacgaataa | 2340 |
| tgcggtctta gtgtctggga tgcacgtcaa tgagattaca ccggcgcaaa tgcgcgcggc | 2400 |
| aatgctaatg gcacatgaac taggagtcgc tttagccaaa tggttaaaag cacatccaga | 2460 |
| tcaaacccaa gtggttacct atgctaaata a | 2491 |

<210> SEQ ID NO 10
<211> LENGTH: 2247
<212> TYPE: DNA
<213> ORGANISM: Bacillus megaterium

<400> SEQUENCE: 10

| | |
|---|---|
| atgaaaatag ctgtaggaat cacaggagcc acgggagcta ttttaggtat tcgaatttta | 60 |
| gagctgttaa agaaggcttc tgttgaaacg catttagtca tgtcgccttg ggctcatgcc | 120 |
| acaattaagc tggaaacatc ctatagcgtt cagcaagtag aagcgctagc agattattgt | 180 |
| tattcatatc aagaccaagc agcaaaaatt tcgagcggct cttttcgtat agatggaatg | 240 |
| attgttagtc cttgcagtat gaaaacatta gcatctattc gaatgggact agcagataac | 300 |
| ttaatagcga aacggcaga tgtgatgtta aagagagaa agccacttgt gctacttcct | 360 |
| cgcgaaacgc ctttaaatac gattcattta gaaaacatgc tggatctttc aaaaatggga | 420 |
| gctatcctgg tgccgcctat gccggctttt tataacaaac taagacgat cgacgatatt | 480 |
| gtcacacata ttgctgttcg aacgttagat cagttgggaa ttgagcttcc tgaagcaaaa | 540 |
| agatggcaag gaattaaaca tttatcacaa ggaggaaaat aaaaatggct tataaagact | 600 |
| ttagagattt ccttgatacg ctacataaag aagggcagct gctgacgatt actgatgaag | 660 |
| tgcagcctga tcctgatttg ggttcagcag gtcaagccat cagtaattta ggagatcaaa | 720 |
| cgccgggatt attgtttact aatatttatg gatatcacaa tgcaaggta gctctaaacg | 780 |
| taatgggttc ctggtcaaat cacgcgttaa tgatggggct gcctaaatcg actcctgtaa | 840 |
| agaacagtt ctttgagttt gctcggagat atgaaaaatt tcctgtcaaa gtgaaaagag | 900 |
| aagagacagc gccgtttcat gagtgtgaaa taacagacga tattaactta ttcgatcttt | 960 |
| tgccgttgtt tcgcttaaat caaggagacg gaggctatta tctagataaa gcgtgtgtta | 1020 |
| tttctcgtga tcagcatgat aaggagaact tcggtaaaca aaatgtaggg ataccgta | 1080 |
| tgcaggtcaa agggaaagat cgtctaggca ttcagcccgt gccacagcat gatattgcca | 1140 |
| ttcatttaaa acaagccgaa gaaaaggtg aaaacctccc tgtatcaatt gctttaggat | 1200 |
| gtgaacctgc gattgttaca gcagccgcta cgccgcttca ttacgatcaa tctgagtatg | 1260 |
| aaatggcagg agctattcaa ggtgagccgt acagaattgt gaagtctcag ctttctgatt | 1320 |
| tagatgtacc ttggggagca gaagtgattt tagaggaga atttttagct ggtgaacgtg | 1380 |
| aatatgaagg tccttttggc gaatttacag gtcattactc aggcggcaga agcatgcctg | 1440 |
| ttatcaaaat caatcatgta taccatcgca agatcctat ttttgaaagt ttatatatcg | 1500 |
| gtatgccttg gacagaaaca gattatttaa ttggaattaa tacaagcgtt cctttatatc | 1560 |
| agcagctaaa agaagcatat cctgaagaga ttgaagctgt gaatgcgatg tatactcatg | 1620 |
| gtctcgttgc tatcatttca acgaaaagcc gatacgagg atttgctaag gcggttggta | 1680 |
| tgagggcatt gactacgccg catggattag atattgcaa gctagttatt ttagtagacg | 1740 |
| aagatgtgga tccgttttaat ttaccgcaag tcatgtgggc gctatcaaca aaaatgcacc | 1800 |
| caaaacacga tgttataaca gtgcctaatc tttcagttct gccacttgat ccaggatctg | 1860 |

| | |
|---|---|
| agccggctgg tattacagat aaaatgattt tggatgctac aacaccagtt gcaccggaaa | 1920 |
| caagaggcca ctattctcag cctttagata caccacttga aactgaaaaa tgggaaaaaa | 1980 |
| tcttaacgaa tatgatgcaa aaataaacaa ggaggaatcg acatgcatac ttgtccaaga | 2040 |
| tgtgaagcca acaagcgaa cttagtatct aaatcaccag ttgaaggagc ctgggagatt | 2100 |
| tacttatgca acgtgtgttt gtttacctgg cgttcttctg aacctgagac catcaccaat | 2160 |
| cctgaaaaat accctcgacc atttaaagtc aatccaaaag acgtaccgct ggcaacgcac | 2220 |
| gtgcctcctg tgccaccccg atcttaa | 2247 |

<210> SEQ ID NO 11
<211> LENGTH: 2252
<212> TYPE: DNA
<213> ORGANISM: Bacillus licheniformis

<400> SEQUENCE: 11

| | |
|---|---|
| atgaacatca tcgtcggaat cacgggcgcg accggcgcgg tatttggcgt gcggatgctg | 60 |
| gagtggctga agaaaaccga cgcagagaca caccttgtca tctctccgtg ggcagcggca | 120 |
| acgatcctgc acgaaacggg atatacgatg aaagacgtgg aaaagctcgc atcttttacg | 180 |
| tattcccaca aagaccaggc ggcccgcatt tcaagcggtt cctttcaaac ggacggaatg | 240 |
| attgtcgcac cgtgcagtat gaagacgttg gcgggcatcc gcaccggtat ggcggataac | 300 |
| ctcttgaccc gttcggcgga cgtcatgctg aaggaacgga aaaagctcgt tctgttaaca | 360 |
| agggagacgc cgctgaacca gattcatctt gaaaacatgc ttgagctgac aaaaatgggg | 420 |
| gcggtgatcc tgccgccgat gccggctttt tataatcatc cccaaaatct gaccgaaatg | 480 |
| gtcgatcata tcgtatttcg gacgctggac caatttggca tccatctgtc tgaagcgaag | 540 |
| cgctgggaag gtatgaaaca ggagaaataa ggaggataac agaatggctt atcaagattt | 600 |
| tagagatttt ttaaatacgc tgaaaaaaga aggacagctt cttgaagtcc aggaagaggt | 660 |
| gaagccggaa cccgatttgg gagcagctgc acgcgccgcc aacaacctcg agacaaatc | 720 |
| acccgctctt ttattcaaca acatttacgg ctataacaat gcccaaatcg gctgaatgt | 780 |
| aatcggctcc tggccgaacc acgcattaat gctcggcctt ccaaaagaca cgccggttaa | 840 |
| agaacaattc tttgagttcg cgcgccgtta taatcagttt ccagtaaaag tgcaaagaga | 900 |
| ggagacagcg ccgtttcacg aaaacgaaat cacagaagac atcaacctgt ttgacattct | 960 |
| gccgctcttc cgcatcaatc agggcgacgg cggcttttat ttagacaagg catgcgtcat | 1020 |
| ttcgagagat gtcgaggatc cggaccactt cggcaagcaa aacgtcggca tgtacagatt | 1080 |
| gcaggtaaaa ggcaaagacc gcctcggcat tcagcccgtc ccgcagcatg acattgcgat | 1140 |
| ccacctgcgt caggctgaag agcgcggcga aaacctgcct gtcacgattg cgtcggctg | 1200 |
| cgaaccggtt attgcaacgg cggcatccac accgctctta tacgatcaat cagaatacga | 1260 |
| gatggcaggg gccctgcaag gcgaaccata taaaatcgtc aaatcaaaac tgtctaactt | 1320 |
| agatatccca tggggcgcag aagtggttct cgaaggtgag atccttgcgg gcgaacgcga | 1380 |
| gtatgaaggt ccgttcggcg agtttaccgg ccactattca ggcggacgaa gcatgccgat | 1440 |
| catcaaaatc aagcgcgtct gccaccgcaa caatccgatt tttgaacacc tgtatttagg | 1500 |
| catgccttgg actgaggttg actatatggt cggcattaat acatgtgtgc cgcttaccca | 1560 |
| gcagcttaaa gaggcgtatc cgaatgaaat tgtcgcggta aacgcgatgt atacgcacgg | 1620 |
| cttgatcgcc attgtatcaa cgaaaagccg ctacggcgga ttcgccaaag ccgtcggcat | 1680 |
| gcgcgcgctg acaactccgc acggcctcgg ctactgcaaa atggtgatcc tcgttgacga | 1740 |

| | |
|---|---:|
| agacgtcgat ccgtttaacc tcccgcaagt gatgtgggca atctcaacga aaatgcatcc | 1800 |
| gaaacacgat gcagtcatca tcccggattt atccgttttg cgctagatc caggttctga | 1860 |
| accggcggga atcacccaca aaatgatatt ggacgcgaca acgccggctg caccggaaac | 1920 |
| aaggggacac tattcacagc cgctcgattc ccctatagga acgaaagagt gggaagcaaa | 1980 |
| attaatgaat ctgctaaatc aataaaagag gagagtgttt catcatgcat acatgtccgc | 2040 |
| gctgcgactt aaaaaaagcg gaaaccgtca gcaaatcacc cgttgaagga gcctgggaag | 2100 |
| tctatcaatg ccagcactgc ttttcactt ggaggtcatc agagccggag acgatcacaa | 2160 |
| atcctgaaaa atacaatccg gccttaaaa tcgatcccgc tgaagttgaa acagctgtac | 2220 |
| aagtgccggc gattccagac cggaaaatct aa | 2252 |

<210> SEQ ID NO 12
<211> LENGTH: 2249
<212> TYPE: DNA
<213> ORGANISM: Bacillus atrophaeus

<400> SEQUENCE: 12

| | |
|---|---:|
| atgaaactcg ttgtcgggat gaccggagct acaggggcta ttttcggagt caggcttta | 60 |
| gaatggctga aggccgcagg agcggaaact caccttgtcg tttctccttg ggctcatgtc | 120 |
| acaatcaaac atgaaacagg ttatagctta aagaagttg aagagcttgc ctcatatacg | 180 |
| tactctcata aggatcaggc ggctgccatt tcaagcgggt cttttcaaac ggacggcatg | 240 |
| atcgtcgccc cgtgcagtat gaagtcgctc gcaagcattc gcacggggat ggcggacaat | 300 |
| ctgttgaccc gggctgcaga tgtcatgctg aaagagagaa aaaagcttgt cctgctgacg | 360 |
| agagaaacgc cgcttaacca gattcattta gagaatatgc tcgcattaac aaagatggga | 420 |
| accattattc ttccgccaat gccggctttt tataatcagc cggcaagtct ggatgaaatg | 480 |
| gtggaccata ttgtattcag aacgctggat caattcggca ttcgccttcc tgaggcaaaa | 540 |
| cgctggaatg gaattgaaaa agaaaaagga ggagcttgat catggcttat caagatttca | 600 |
| gagaatttct cgctgccctg gaaaagagg gacagctatt aaaagtggat gaagaggtga | 660 |
| agccggagcc ggatttagga gccgcagccc gcgcagccaa caacctcggc gataaaagcc | 720 |
| cggctctttt atttaacaat atttacggct acaacaatgc acaaatcgcg atgaatgtca | 780 |
| tcggttcttg gccgaaccac gcgatgatgc ttggcttgcc gaaagataca ccggtgaaag | 840 |
| agcagttttt tgaatttgcg aagcgatatg aacagtttcc gatgccggtc aaacgcgaag | 900 |
| aaactgcacc atttcatgaa aatgaaatca cagaggacac caacctgttc gatctattgc | 960 |
| ctcttttcag aattaaccag ggtgacggcg gctattattt agataaagcg tgtgtcattt | 1020 |
| cccgtgatct ggatgaccct gacaatttcg gcaagcagaa cgtcggaatt taccggatgc | 1080 |
| aggtaaaagg gaaagaccgc ctcggcattc agccagttcc gcagcatgac atcgcgattc | 1140 |
| atcttcgcca agcagaagaa cgcggcgtca atcttccggt cactatcgcg cttggctgtg | 1200 |
| agcctgtcat tacgaccgcg gcgtcaactc cgctcctata tgaccaatca gaatacgaaa | 1260 |
| tggcgggagc gatccaaggc gaaccgtata gaatcgtcaa atcaaacctg tctgaccttg | 1320 |
| atattccttg gggcgcagaa gtcgtgcttg aaggagaaat cattgccgga gaacgggaat | 1380 |
| atgaaggacc gttcggcgaa tttaccggcc attattcagg cggacgcagc atgccgatta | 1440 |
| tcaaaatcaa acgcgtatct catagaaatc atccggtatt tgaacattta tatctcggca | 1500 |
| tgccttggac agagtgcgat tacatgatcg gcattaatac atgcgtgccg ctttatcagc | 1560 |

-continued

| | | | | |
|---|---|---|---|---|
| agctgaaaga | agcatatccg | agtgaaattg | tcgctgtgaa | cgcaatgtac acacatggct | 1620 |
| taatcgccat | tgtatctgca | aaaacccgtt | acggaggatt | tgcaaaagct gtcggaatga | 1680 |
| gagccctgac | tacaccgcac | ggactcggct | actgtaagat | ggtgatcgtc gtggatgaag | 1740 |
| atgttgatcc | gttcaacctc | ccgcaagtca | tgtgggcgct | tcaacaaag atgcatccga | 1800 |
| agcatgatgc | cgtaaccatt | cctgatttat | ccgtgctgcc | gcttgatccg ggatcagacc | 1860 |
| catccggcat | tactcataaa | atgattctcg | atgccacaac | gcctgttgcg ccggaaacaa | 1920 |
| gaggccatta | ttcacagccg | cttgactctc | ctttaacaac | aaaagaatgg gaacaaaaac | 1980 |
| taatggactt | gatgaataaa | taagagaaag | gatgatctga | catgcataca tgtcctcgat | 2040 |
| gtgattcaaa | aagggagaa | tcatgagca | atcgcctgt | agaaggcgct tgggaagtct | 2100 |
| accaatgtca | aacgtgtttc | ttcacatgga | gatcatgtga | accggaaagc attcaaaacc | 2160 |
| cgaaaaaata | caatccatca | tttaagatcg | atccgaagga | aacagaaaca gctgttgaag | 2220 |
| tgccggctgt | tccggaaaga | aaggcctga | | | 2249 |

<210> SEQ ID NO 13
<211> LENGTH: 2283
<212> TYPE: DNA
<213> ORGANISM: Bacillus subtilis subsp. subtilis

<400> SEQUENCE: 13

| | | | | |
|---|---|---|---|---|
| atgaaagcag | aattcaagcg | taaaggaggg | ggcaaagtga | aactcgttgt cggaatgaca | 60 |
| ggggcaacag | gggccatttt | cggggtcagg | ctgctgcagt | ggctgaaggc cgccggagtg | 120 |
| gaaacccatc | tcgttgtgtc | tccttgggca | aacgtcacga | tcaaacacga aacaggctat | 180 |
| acgttacaag | aagtagaaca | actggccaca | tacacttact | cacataagga tcaggcggca | 240 |
| gccatttcaa | gcgggtcgtt | tgataccgat | ggaatgattt | tgcgccgtg cagcatgaaa | 300 |
| tctctcgcaa | gcattcgcac | aggaatggcg | gataatctgc | tgacacgtgc ggcggatgtc | 360 |
| atgctcaagg | agagaaaaaa | actcgtcctc | ttaacgagag | agacgccttt gaaccaaatt | 420 |
| catctcgaaa | atatgctagc | gcttacgaaa | atgggcacca | tcattcttcc tccgatgccg | 480 |
| gcattttata | tcggccgag | aagcttagag | gaaatggttg | accatattgt ttttagaacg | 540 |
| ttggaccaat | tcggcattcg | gcttcctgaa | gcgaagcgct | ggaatgggat tgaaaaacaa | 600 |
| aaaggaggag | cttgatcatg | gcttatcaag | atttcagaga | atttctcgct gcccttgaaa | 660 |
| aagaaggaca | gctgcttaca | gtgaatgaag | aggtaaagcc | ggaaccggat ttaggggcct | 720 |
| ccgcacgggc | agccagcaat | cttggcgata | aaagccctgc | gctcttattt aacaacattt | 780 |
| acggctatca | taacgcgcga | attgcgatga | atgtcatcgg | ctcttggcca aaccatgcca | 840 |
| tgatgctggg | catgccgaaa | gacacaccgg | taaagaaca | gttttttgaa ttcgcaaagc | 900 |
| gttatgacca | gtttccgatg | ccggtcaaac | gtgaggaaac | agcgccattt catgaaaatg | 960 |
| aaatcacaga | agatatcaat | ttgttcgata | tactgcctct | tttcagaatt aaccagggtg | 1020 |
| atggaggcta | ctatttagac | aaagcatgtg | tcatttcccg | tgatcttgag gaccctgaca | 1080 |
| acttcggcaa | acaaaatgtc | ggcatttaca | gaatgcaagt | caaggaaaa gaccgccttg | 1140 |
| gcattcagcc | tgtcccgcag | cacgatattg | caatccatct | gcgccaagct gaagaacgcg | 1200 |
| gcatcaacct | tccggtcact | attgcgctcg | gctgtgagcc | ggtcattaca acggcggcat | 1260 |
| cgactccgct | tctctatgat | caatcagaat | acgaaatggc | aggtgcgatt caaggcgaac | 1320 |
| catatcgcat | cgtcaaatca | aagctgtctg | atcttgatgt | tccgtggggc gctgaagtgg | 1380 |
| tgcttgaagg | tgagattatt | gccggagagc | gcgaatatga | agggccgttc ggtgaattca | 1440 |

```
caggccatta ttccggcgga cgcagcatgc cgattatcaa aattaaacgc gtctatcaca    1500
gaaacaatcc gatctttgaa catttatact taggcatgcc ttggacagaa tgcgattaca    1560
tgatcggcat taacacatgc gtgccgcttt atcagcagtt aaaagaagcg tatccgaacg    1620
aaattgtggc agtgaacgcc atgtacacac acggtttaat cgcgattgtt ccacaaaaa    1680 cccgctatgg cggatttgcg aaagcggtcg gcatgcgcgc actcacaacg ccgcacggac    1740
tcggctactg caaaatggtc atagtcgttg atgaggatgc cgatccattc aaccttccgc    1800
aggtcatgtg ggcgctttcg accaaaatgc atccgaaaca tgatgcggtc atcattccgg    1860
acttatctgt cctgccgctt gatccgggat ccaatccatc aggaatcact cacaaaatga    1920
ttctcgacgc cactacaccg gttgcgccgg aaacaagagg ccattattca cagccgcttg    1980
attctccgct aacaacgaaa gaatgggaac aaaaactaat ggacttaatg aataaataag    2040
gaaaggatgt tcgaaatgca tacatgtcct cgatgcgact caaaaaaggg agaagtcatg    2100
agcaaatcgc ctgtagaagg cgcatgggaa gtttatcagt gccaaacatg cttttttaca    2160
tggagatcct gtgaaccgga aagcattaca aatcccgaaa aatacaatcc agcgtttaaa    2220
attgatccaa aggaaacaga aacagcaatt gaagttccgg cggtgccgga acgaaaggct    2280
tga                                                                   2283

<210> SEQ ID NO 14
<211> LENGTH: 2283
<212> TYPE: DNA
<213> ORGANISM: Bacillus subtilis subsp. spizizenii

<400> SEQUENCE: 14
atgaaagcag aattcaagcg taaaggaggg ggcaaagtga aactcgttgt cggaatgaca      60
ggggcaacag gggctatttt cggggtcagg ctgctggagt ggctgaaggc ggccgaagta     120
gaaacccatc tcgtcgtgtc tccttgggct aacgtcacga tcaaacgaca aacaggctat     180
accttaaaag aagtagaaca acttgccaca tacacgtatt cgcataagga ccaggcggca     240
gccatttcaa gcgggtcgtt tgataccgat ggcatgattg ttgcgccatg cagcatgaaa     300
tctctcgcaa gcattcgcac cgggatgcg gataatctgc tgacgcgtgc ggcggatgtc     360
atgctcaagg agagaaaaaa actcgtcctc ttaacgagag agacgccttt gaaccagatt     420
catctcgaaa atatgctagc gcttacgaaa atgggtacca tcattcttcc tccgatgccg     480
gcattttata tcagccgag cagcttagag gaaatggttg accatattgt attcagaacg     540
ttggaccaat tcggcattcg ccttcctgaa gcgaaacgct ggaatgggat tgaaaaacaa     600
aaaggaggag cttgatcatg gcttatcaag atttcagaga atttctcgct gcccttgaaa     660
aagaaggaca gctgctaaca gtgaatgaag aggtaaagcc ggagccggat ataggggctg     720
cagcacgcgc agccagcaat cttggcgata aaagccccgc gctcttattt aataacattt     780
atggctatca caacgcgcaa attgcgatga atgtgatcgg ctcctggccg aaccatgcaa     840
tgatgctggg catgccgaaa gacacgccgg tgaaagaaca gttttttgaa tttgcgaaac     900
gttatgacca gtttccgatg ccagtcaaac gtgaggaatc agcgccgttt catgaaaatg     960
aaatcacaga agatatcaat ttgttcgata tactgcctct tttcagaatt aaccaaggag    1020
acggcggtta ctatctagac aaagcatgtg tcatttcccg cgatcttgaa gatcctgaga    1080
atttcggcaa acaaaacgtc gggatttaca gaatgcaggt caaaggaaaa gaccgccttg    1140
gcattcagcc tgtgccgcag cacgatattg cgatccatct gcgtcaagct gaagaacgcg    1200
```

-continued

```
gcatcaatct tccggtcacc attgcgctcg gctgtgagcc ggtcataaca acggcggcat      1260
cgactccgct tctttatgat caatcagaat acgaaatggc aggcgcaatt caaggtgaac      1320
catatcgcat cgtgaaatct aagctgtctg atcttgatgt tccatggggc gctgaagtag      1380
tgcttgaagg tgaaatcatt gccggagagc gtgaatatga aggcccgttc ggtgagttca      1440
caggccatta ttccggcgga cgcagcatgc cgattattaa aattaaacga gtgtatcata      1500
gaaacaatcc gattttgaa catttatact taggcatgcc ttggacagaa tgcgattaca       1560
tgattggcat taacacttgt gtgccgcttt atcagcagtt aaaagaagcg tatccgaatg      1620
aaattgtggc tgtgaacgcc atgtacacac acggtttgat cgcgattgtt tccacaaaaa      1680
cacgctatgg cggatttgcg aaagcagtcg gcatgcgcgc gctcacaaca ccgcacggac      1740
tcggctactg caaaatggtc attgtcgttg acgaggatgt cgatccattc aatctgccgc      1800
aggtcatgtg ggcgctttcg accaaaatgc atccgaagca cgatgcggtc atcattccag      1860
acttatctgt cctgccgctt gacccgggat ctaatccatc aggaatcact cacaaaatga      1920
ttcttgacgc cactacaccg gttgcgccgg aaacaagagg ccattattca cagccgcttg      1980
attcaccatt aacaacgaaa gaatgggaac aaaaactaat ggacttaatg aataaataag      2040 aaaggatga tcgaaatgca tatatgtcct cgttgcgatt cgaaaaaggg agaagtcatg       2100
agcaaatcgc ctgtagaagg cgcatgggaa gtttatcagt gtcaaacatg ttttttcaca      2160
tggagatcct gtgagccgga aagtattaca aatccggcga aatacaatcc agcgtttaaa      2220
attgatccga aggaaacaga aacagcaatt gaagttccgg ctgtgccgga acgaaaggct      2280
tga                                                                    2283
```

<210> SEQ ID NO 15
<211> LENGTH: 2268
<212> TYPE: DNA
<213> ORGANISM: Enterobacter aerogenes

<400> SEQUENCE: 15

```
atgaaactga ttattgggat gaccggggcg accggcgcgc cgttaggcgt cgcgctgtta       60
caggcgctga tgaaaatgcc ggatgtggaa acgcatctgg tcatgtcgaa atgggcaaaa      120
accaccattg agctggaaac gccctatagc gctcgtgatg tcgccgcgct ggcggacttc      180
tgccatagcc ctgcggatca ggccgcgacc atctcatcag gatcgtttcg taccgacggc      240
atgattgtta tcccctgcag catgaaaacg ctggcgggta ttcgcgctgg ctatgcggaa      300
gggttagtcg gccgcgcggc ggacgtggtg ctgaaagagg ggcgcaagct ggttctggtg      360
ccgcgtgaaa tgccgctgag caccattcat ctggagaaca tgctggcgct gtcgcgcatg      420
ggcgtggcga tggtgccgcc catgcctgcc tattacaacc acccggaaac ggtagaggat      480
atcaccaacc atatcgtgac ccgggtgctg atcagtttg gtctcgaata tcacaaagcg      540
cgccgctgga acggcctgcg cgcggtcgag aatttatcac aggagaatta atcatggctt      600
ttgatgattt acgcagcttt ttgcaggcgc ttgatgagca gggcaactg ctaaaaatta      660 gcgaagaggt gaatgccgag ccggatctcg ccgctgccgc taacgccaca gggcgcatcg      720
gtgacggcgc gccagcgttg tggtttgata acattgcgg ctttaccgac gcccgtgtcg       780
ccatgaacac catcggttcc tggcaaaacc acgcgatttc gctgggggctg ccgccaaaca     840 cgccggtgaa aaagcagatt gatgaattta ttcgccgctg gataaattc ccggtaacgc       900 cggagcgtcg cgctaatcca gcgtgggcgg aaaaacaccgt tgatgcgac gatatcaacc      960 tgttcgatat tctgccgctg ttccgcctga acgatggcga cggtggtttc tatctcgaca     1020
```

-continued

```
aagcctgtgt ggtttcgcgc gatccgcttg acccggacca ctttggcaaa cagaacgtcg    1080
gtatttaccg gatggaagtg aaaggcaagc gcaagctggg cctgcagccg gtaccgatgc    1140
acgatatcgc gctgcatctg cataaagcgg aagagcgcgg tgaggatctg cccattgcca    1200
tcaccctggg taacgacccg attattaccc tgatgggcgc gacgccgctg aaatatgacc    1260
agtcagaata tgagatggcg ggcgcgctgc gcgaaagccc gtatcccatc gccaccgcgc    1320
cgctgaccgg ctttgacgtt ccctgggggct cagaggtgat ccttgaaggg gtgattgaag    1380
ggcgcaagcg tgaaatcgaa gggccgttcg gcgagttcac cggccactac tcaggcggcc    1440
gcaatatgac ggtggtgcgt atcgataaag tctcttatcg cacaaaaccg attttttgaat    1500 cgttgtatct cggaatgccg tggaccgaaa tcgactatct gatgggcccg gcgacctgcg    1560
tgccgctgta ccagcagctg aaggcggagt tcccggaggt gcaggcggtc aatgccatgt    1620
acacccatgg tctgctggcg attatctcca ccaaaaaacg ctacggcggt tttgcccgcg    1680
cggtgggatt acgggcaatg actaccccgc acggcctcgg ttacgtgaaa atggtgatca    1740
tggtcgatga agatgtcgat ccgttcaacc tgccgcaggt gatgtgggcg ctctcctcga    1800
aggtcaaccc ggcgggcgac ctggtacagt tgccgaacat gtcggtgctg gagcttgacc    1860
ctggttccag tccggcgggg atcaccgaca aactgattat cgacgccacc accccggttg    1920
cgcctgacct tcgcggtcac tacagccagc cggttcagga tttaccggaa accaaagcct    1980
gggctgaaaa actgaccgcc atgttggcca accgtaaata aggagaagaa gatgatttgt    2040
ccacgttgcg ctgatgagca gattgaagtg atggcgacgt cgccggtaaa agggtgtgg    2100 atcgtttacc agtgccagca ctgcctctat acctggcgta ataccgaacc gctgcgtcgt    2160
accagccgcg aacattatcc ggaagcgttc cgcatgacgc agaaagatat tgatgaggcg    2220
ccgcaggtgc cgcatattcc accgctgttg gcggcagata agcgttaa              2268
```

<210> SEQ ID NO 16
<211> LENGTH: 2252
<212> TYPE: DNA
<213> ORGANISM: Enterobacter cloacae

<400> SEQUENCE: 16

```
atgagattga tcgtgggaat gacgggagca acaggtgctc cgctgggtgt ggctttactg      60
caggcgttac gtgacatgcc agaggttgaa acccatctgg tgatgtcgaa atgggcgaaa     120
accaccattg agctggaaac gccttatacc gcgcaggatg tcgccgccct ggcagatgtc     180
gttcacagtc ctgccgatca ggctgccacc atctcctccg gctcgtttcg taccgacggc     240
atgatcgtca ttcccctgcag catgaaaacg ctggcgggta tccgcgcggg ctatgccgaa     300
gggctggtgg gccgtgcggc agacgtggtg ctgaaagagg ggcgcaagct ggtgctggtc     360
ccgcgtgaaa cgccgctcag caccattcat ctggagaaca tgctcgcgct ttcccgcatg     420
ggggtggcga tggtgccgcc catgcctgcg tattacaacc cccgcaaac cgccgatgat     480 atcacccagc atatcgtgac ccgcgtactc gaccagtttg gtctggagca caaaaaggcg     540
cgtcgctgga acggcctgca ggcggcgaaa cattttttcac aggagaataa cgatggcatt     600
tgatgatttg agaagcttcc tgcaggcgct agatgagcaa gggcaactgc tgaaaattga     660
agaagaggtc aatgcggagc cggatctggc ggcggccgct aacgcgacgg gacgtatcgg     720
tgatggtgcg cctgcgctgt ggttcgataa cattcgcggg tttaccgatg ccagggtggt     780
gatgaacacc atcggctcct ggcagaacca cgccatttcg atgggggctgc cggcgaatac     840
```

```
cccggtcaaa aagcagatcg atgagtttat tcgccgctgg gataaattcc cggtcgcacc    900
ggagcgccgg gccaacccct catgggcgca gaatacggtg gacggtgagg agattaacct    960
gttcgacatc ctgccgctgt ttcgcctgaa cgacggggac ggcggttttt atctcgacaa   1020
agcgtgcgtt gtctcgcgcg atccgctcga cccggaccat ttcggcaagc agaacgtcgg   1080
tatttaccgc atggaagtga agggcaaacg taagctcggc ctgcagccgg tgccgatgca   1140
tgatatcgcc ctgcatctgc ataaagccga agagcgtggt gaagacctgc cgattgcgat   1200
tacgttgggc aacgatccga tcatcaccct gatgggcgca acgccgctga atacgatca    1260
gtccgagtat gaaatggccg gggcgctgcg tgaaagcccg tacccgattg cgaccgcgcc   1320
gttgaccggc ttcgatgtgc cgtggggtc tgaagtgatc ctggaagggg tgattgaagg    1380
ccgtaaacgt gaaattgaag gccgttcgg tgagtttacc gggcactatt cgggcggacg    1440
caatatgacg gtggtccgta ttgataaagt ctcgtaccgc accaaaccga ttttcgaatc    1500
cctctatctc gggatgccct ggaccgagat cgactacctg atgggccagc ccacctgtgt   1560
gccgctttac cagcaactga aagcgagttt ccctgaagtg caggcggtga acgcgatgta   1620
tacccacggt ctgctggcga tcatctccac caaaaaacgc tacggtggtt ttgcccgcgc   1680
ggtcggttta cgcgccatga ccacgccgca tggcctgggc tatgtgaaga tggtgattat   1740
ggtggatgaa gatgtcgatc cgttcaacct gccgcaggtg atgtgggcgc tgtcatcaaa   1800
agtgaacccg gcaggggatc tggtgcagct gccgaacatg tcggttcttg agcttgatcc   1860
tgggtccagc ccggcaggca tcaccgacaa gctgattatt gatgccacca cgcctgttgc   1920
gccggataac cgcggtcact acagccagcc ggtgcaggat ttacctgaaa ccaaagcctg   1980
ggctgaaaag ctgactgcga tgctggcagc acgccaataa ggaggaaaag atgattgtc    2040
cacgttgtgc cgatgagcaa attgaggtga tggcccacatc accggtgaaa gggatctgga   2100
cggtttatca gtgccagcat tgcctgtata cctggcgcga tactgagccg ctgcgtcgta   2160
ccagccgcga acattaccct gaagcgttcc gcatgacgca aaggatatt gatgaggcgc    2220
cgcaggtacc gaccattccg ccattgctgt aa                                 2252

<210> SEQ ID NO 17
<211> LENGTH: 2284
<212> TYPE: DNA
<213> ORGANISM: Enterobacter sakazakii

<400> SEQUENCE: 17
atgaggctaa ttgtcggaat gacgggcgca accggcgcgc cgcttggggt cgcgctgttg     60
caggcgctga aagcgatgcc tgaggtggaa acccatctgg tgatgtcaaa gtgggcgaaa    120
accacgatcg aactggaaac gccgttctcc tggcaggatg tcgcggggct ggcagatgtg    180
gtgcacagcc cggcggatca ggccgcgacg atctcctcag gatcgtttcg caccgacggc    240
atggtgatca ttccgtgcag catgaaaaac ctggcgggca tccgcgcggg ctacgccgac    300
gggctggtgg gccgcgccgc tgatgtggtg ctgaaagaga accgtaaact ggtgctggtg    360
ccgcgcgaaa caccgcttag caccattcat ctggaaaacc tgctggcgct ctcgaagatg    420
ggcgtggcca tcgtgccgcc catgcccgcc tggtacaacc atcccgcgac gatcgacgac    480
atcatcaacc atatcgtcgc gcgcgtgctc gatcagttcg ggctcgatgc ccgcaacgcc    540
cgccgctggc agggctaaa tcctgcgaaa acagccgaca cccattcatc acgaggagga    600
aacacgcatg gcgtttgacg atctgcgcag cttttttgcag gcgcttgaag agcaggggca    660
actgctgagg atcagcgaag aggtgcaggc ggagccggat atcgcggcgg ccgccaacgc    720
```

-continued

```
gaccggacgc atcggcgaag gcgcgcccgc gctctggttt gacaatatcc gcggctttac      780
tgacgcgcgg gtggcgatga acaccattgg ttcatggccg aaccacgcga tctcgctcgg      840
tctgccgcct gccacaccgg taaagcagca gatagaagaa tttattcgcc gctgggatac      900
cttcccggtc gcgccggaac gccgcgataa tccgccatgg gcggaaaaca cgtcgacgg       960 cgacgacatt aacctgttcg acattctgcc gctgtttcgc ttaaacgacg gcgacggcgg     1020
gttctacctt gataaagcgt gtgtggtctc gcgcgatccg ctcgatcccg aacacttcgg     1080
caagcagaat gtcggcatct accggatgga agtgaaaggc aagcgcaagc tcgggctgca     1140
accggtgccg atgcatgaca cgcgctgca tctgcataag gccgaagagc gtggcgagga      1200
tttgccggtt gcgattacgc ttggcaacga tccgatcatc acgctgatgg gcgccacgcc     1260
gctgaaatac gatcagtcgg aatatgaaat ggcgggcgcg ctgcgcgaaa gcccgtaccc     1320
gatagccacc gcgccgctga ccggtttcga cgtgccgtgg gggtcggaag tgatccttga     1380
aggggtgatt gaaggacgca agcgcgagat agaagggccg ttcggcgagt ttaccgggca     1440
ctactccggc gggcgtaaca tgaccgtggt gcgtatcgat aaagtctctt atcgcaccaa     1500
accgattttc gaatcgctct atctcggcat gccgtggacc gaaatcgact acctgattgg     1560
cccggcgacc tgcgtgccgc tttaccagca gcttaaagcg gagttcccgg aagtgcaggc     1620
ggtgaacgcg atgtataccc acgggctgct cgcgattatc tccaccaaga aacgctacgg     1680
cggtttcgcc cgcgcggtgg gcctgcgtgc gatgaccacg ccgcacgggc ttggctacgt     1740
gaagatggtg attatggtgg atgaggatgt cgatccgttc gatctgccgc aggtgatgtg     1800
ggcgctgtcg tcaaaagtga acccggcggg cgatctggtg cagttgccga atatgtcggt     1860
gctggagctt gatcctggct caagcccggc ggggattacc gacaagctga ttatcgacgc     1920
cactacgccg gttgcgccgg ataaccgcgg gcattacagc cagccggtga agacctgcc      1980 ggaaaccccg cagtgggtag agaagctgac cgccatgctg gctaaccgta aaaaataagg     2040
agacgagatg atttgtccac gttgtgccga tgaaaccatc gaaatcatgg cgacgtcgcc     2100
ggtgaaaggc gtctggacgg tgtatcagtc ccagcattgt ttgtacacct ggcgcgacac     2160
cgagccgctg cgccgtacca gccgcgagca ttaccccgag gcgttccgga tgacgcaggc     2220
cgatatcgat aacgcgccgg aagtgccaac ggtgccgccg ctgctggcgg atggtaagcg     2280
ttaa                                                                   2284
```

<210> SEQ ID NO 18
<211> LENGTH: 2252
<212> TYPE: DNA
<213> ORGANISM: Enterobacter hormaechei

<400> SEQUENCE: 18

```
atgagattga ttgtgggaat gacgggcgcg acgggtgcgc cattaggcgt ggcgttgttg       60
caggcgctgc gggaaatgcc ggaggtggaa acgcacctgg tgatgacgaa gtgggcaaaa      120
accacgattg agctggaaac gcccttcact gcgcatgacg ttgctgcact ggcggatgtc      180
gtccacagtc cggccgatca ggctgccacc atctcctccg gctcgtttcg caccgacggc      240
atgatcgtca tcccgtgcag catgaaaacg ctggcgggga tccgcgcggg ctacgccgaa      300
gggctggtag gcgtgcggc agacgtggtg ctgaaagagg acgcaagct ggtgctggtt        360 ccccgcgaga cgccgctcag caccattcat cttgagaaca tgcttgccct ttcccgcatg      420
ggcgtggcga tggtgccgcc tatgcctgcg tactacaacc acccgcaaac cgccgatgac      480
```

```
attacccagc atatcgtgac ccgcgttctc gaccagtttg gtctggagca taaaaaagcc      540
cgacgctggg aaggtttgca ggcagcgaaa cattttttcac aggagaataa agatggcatt     600
tgatgatttg agaagcttct tgcaggcgct cgatgagcaa gggcagctgc tgaaaattga     660
ggaagaggta aacgcggagc cggatttagc ggcggccgcc aacgctaccg gcgcattgg      720
cgatggcgcg cctgcgctgt ggttcgataa tattcgcggc ttcaccgatg cccgagtggt     780
gatgaacacc atcggctcgt ggcaaaacca cgccatttcg atgggctgc cagcgaatac      840
ttcggtgaaa aaacagatcg acgagtttat tcgtcgctgg acaaattcc ccgtcacgcc     900
agagcgtcgt gccaatcctg cctgggcgca gaacacggtg gacggagaag atatcaacct     960
gttcgacatt ttgccgctgt ccgcctgaaa cgacggtgac gggggctttt atctcgataa    1020
agcgtgcgtt gtctcccgcg atccgctcga ccccgaccac ttcggcaagc agaacgtcgg    1080
catttaccgt atggaagtga agggcaagcg taagctcggc ctgcaaccgg tgccgatgca    1140
tgatattgcg ctgcatctgc ataaggcaga gagcgtggc gaagacctgc ccattgccat     1200
tacgctgggt aacgatccga tcatcaccct gatgggcgcc acgccgctga aatacgatca    1260
atccgagtat gagatggctg gcgcgctacg cgaaagcccg tatccgattg cgacggctcc    1320
gctgaccggt tttgatgtgc cgtgggggtc ggaagtgatc ctggaagggg tgattgaagg    1380
ccggaaacgt gaaattgaag gaccattcgg tgagtttacc ggacactact ctggcgggcg    1440
caacatgacc gttgtgcgca ttgataaagt ctcttaccgc accaaaccca ttttcgaatc    1500
tctctacctg gggatgcctt ggaccgagat tgattatctg atgggacccg ccacctgcgt    1560
gccgctctat cagcaactga aggcggaatt cccggaagtg caggcggtaa acgccatgta    1620
cacccacggt ctgctggcaa ttatctccac taaaaagcgt tacggcggtt ttgcccgtgc    1680
ggtcgggcta cgcgccatga ccacaccgca cggtctgggt tacgtgaaga tggtgattat    1740
ggtggatgaa gatgtcgatc cgtttaacct gccgcaggtc atgtgggcgc tttcatcgaa    1800
ggttaatccg gcgggcgatc tggtgcagct tccgaatatg tctgtgctgg aacttgaccc    1860
tggctccagc ccggcgggga tcaccgacaa gctgatcatt gatgccacca cccctgttgc    1920
cccggacaac cgtggtcact acagccagcc ggtacaggac ctcctgaaa ccaaagcctg     1980
ggccgaaaaa ctgaccgcga tgctggcagc acgtcaataa ggaggaaaaa atgatttgtc    2040
cacgttgtgc cgatgaacat attgaagtaa tggcaacatc accggtgaaa ggtgtctgga    2100
cggtatatca gtgccagcac tgtctgtata cctggcgcga taccgaaccg ctacgccgta    2160
ccagccgcga gcattacccg gaagccttcc gcatgacgca aaggatatt gatgaggcgc     2220
cgcaggtgcc aacaatcccg ccgctgctgt aa                                   2252
```

<210> SEQ ID NO 19
<211> LENGTH: 2268
<212> TYPE: DNA
<213> ORGANISM: Escherichia coli

<400> SEQUENCE: 19

```
atgaaactga tcgtcgggat gacaggggct accggtgcgc tcttggtgt ggcattactg      60
caagcgctgc gggagatgcc gaatgtcgag actcatctgg tgatgtcgaa gtgggcgaaa    120
accaccattg aactggaaac gccttacagc gctcgcgatg ttgctgccct cgcagacttc    180
agccataacc cggcggatca ggcggcgatc atctcatccg gttctttcg taccgacggc    240
atgatcgtta ttccgtgcag tatgaaaacg ctcgccggta tccgcgctgg ttacgccgat    300
ggcctggtag ggcgcgcggc ggacgtcgtg ctcaaagaag gccgcaaact ggtgctggtg    360
```

```
ccgcgtgaaa tgccgcttag caccatccat ctcgaaaata tgctcgcact ttcacgcatg    420
ggcgtggcga tggtgccgcc gatgcctgcc ttttataacc atcccgaaac ggtagatgac    480
attgtccacc atgtggtagc ccgcgtgctg gatcaatttg gcctcgaaca tccccacgcc    540
aggcgctggc aaggattgcc gcaggcccgg aattttctc aggagaatga ataatggcat    600
ttgatgattt acgcagcttt ttacaggcgc ttgatgacca cggccagtta ctgaaaatca    660
gcgaagaagt gaacgccgag ccggatctgg cagcagcagc taacgccacc gggcgtatcg    720
gcgacggcgc gcccgcgctg tggtttgata atattcgcgg ctttaccgat gcccgcgtgg    780
cgatgaacac catcggttcc tggcagaacc acgcgatttc cctcggcctg ccgccaaatg    840
ccccggttaa aaagcagatt gatgagttta tccgccgctg gataacttc ccgattgccc    900 cggagcgccg cgccaatcca gcctgggcgc agaacaccgt tgatggcgac gagatcaacc    960
tgttcgatat cctgccgctg tttcgtttaa cgatggcga tggcggtttc tatctcgaca   1020
aagcgtgcgt ggtttcccgc gatccgctcg accggataa cttcggcaag cagaacgtcg   1080
gcatctaccg catggaagtg aagggcaagc gtaagctcgg cctgcaaccg gtgccgatgc   1140
acgatatcgc cctgcatctg cataaagcag aagagcgcgg tgaagatctg ccgattgcga   1200
tcacgctcgg taacgatccg atcatcacgc tgatggggc cacgccgctg aaatatgatc   1260
agtccgagta cgaaatggca ggcgcgctgc gtgaaagccc gtaccgatc gccaccgccc   1320 cgttgaccgg ttttgatgtg ccgtgggtt cagaagtgat cctcgaaggg gtcatcgaaa   1380
gccgtaaacg cgaaatcgaa gggccgttcg gtgagtttac cggcactac tccggcgggc   1440 gtaacatgac cgtggtgcgc atcgataaag tctcttaccg caccaggccg attttcgaat   1500
cgctgtacct cggtatgccg tggaccgaaa tcgactacct gatggggcca gccacctgcg   1560
tgccgctgta tcagcagctg aaagccgagt ccctgaagt gcaggcggta acgccatgt   1620 acacccatgg cctgctggcg attatctcca ccaaaaaacg ctacggcggc tttgcccgcg   1680
cggtgggcct gcgcgcaatg accacgccgc atggtctggg ctacgtgaag atggtgatta   1740
tggtcgatga agacgttgac ccgttcaacc tgccgcaggt gatgtgggcg ctctcctcga   1800
aagtgaaccc ggcaggggat ttggtgcagt tgccgaatat gtccgtgctg aactcgatc   1860 caggctcaag ccctgcgggg atcaccgaca agctgattat cgacgccact acgcctgtcg   1920
ccccggacaa ccgtggtcac tacagccaac cggtggtgga tttaccggaa accaaagcct   1980
gggctgaaaa actgaccgct atgctggctg cacgtaaata aggagaagaa gatgatttgt   2040
ccacgttgtg ccgatgaaca gattgaagtg atggcgaaat cgccggtgaa agatgtctgg   2100
acggtatatc agtgccagca ttgccttat acctggcgcg ataccgaacc gctgcgccgt   2160
accagccgcg aacattatcc cgaagcgttc cgcatgacgc agaaagatat tgatgacgcg   2220
ccaatggtgc cgagcatccc gccgctgctg gtggaaggta agcgctaa                2268
```

<210> SEQ ID NO 20
<211> LENGTH: 2268
<212> TYPE: DNA
<213> ORGANISM: Escherichia fergusonii
<400> SEQUENCE: 20

```
atgagactga tcgtcgggat gacaggggcc accggagcgc tcttggtgt ggcattactg     60 caagcgctgc gggagatgcc gaatgtcgag actcatctgg tgatgtcgaa gtgggcgaaa   120
accaccattg aactggaaac gccttacaac gcccgcgatg ttgctgccct cgcagacttc   180
```

```
tgccataacc cggcggatca ggccgcaacc atctcctcag gttcctttcg taccgacggt    240
atgatcgtta ttccgtgcag tatgaaaacg ctcgccggta tccgcgctgg ttacgccgat    300
ggcctggtag ggcgcgcggc ggacgtcgtg ctcaaagaag gccgcaaact ggtgctggtg    360
ccgcgtgaaa tgccgcttag caccatccat ctcgaaaata tgctcgcact ttcgcgcatg    420
ggcgtggcga tggtgccgcc gatgcctgcc ttttataacc atcccgaaac ggtagatgac    480
attgtccacc acgtggtagc ccgcgtgctg atcaatttg gcctcgaaca tcctcacgcc    540
aggcgctggc aaggattgcc gcaggcccgg aattttccc aggagaatga ataatggcat    600
ttgatgattt acgcagcttt ttacaggcgc ttgatgacta cggtcagtta ctgaaaatca    660
gtgaagaagt gaacgccgag ccggatctgg cagccgctgc aacgccacc gggcgtatcg     720 gcgacggtgc accggcgctg tggtttgaca atattcgcgg ctttaccgat gcccgcgtgg    780
caatgaacac catcggctcc tggcagaacc acgcgatttc cctcggcctg ccgccaaaca    840
ccccggttaa aaacagatt gatgagttta tccgccgctg ggataacttt cccattgccc    900
cggagcgccg tgcgaatccg gtctgggcgc agaacaccgt cgatggcgac gagattaatt    960
tgttcgatat tctgccgctg tttcgtttaa acgatggcga tggcggtttc tatctcgaca   1020
aagcgtgcgt ggtttcccgc gatccgctcg acccggataa tttcggcaag cagaatgtcg   1080
gcatctaccg catggaagtg aagggcaagc gtaagctcgg cctgcaaccg gtgccgatgc   1140
acgatatcgc cctgcatctg cataaagcag aagagcgcgg tgaagatctg ccgattgcga   1200
tcacgctcgg taacgatccg atcatcaccc tgatggggggc caccccgctg aaatacgatc   1260
aatcagagta cgaaatggct ggcgcactac gcgaaagccc gtacccgatc gccaccgccc   1320
cgctgaccgg ttttgatgtg ccgtggggct cagaagtgat cctcgaaggc gttatcgaaa   1380
gccgtaaacg cgagattgaa gggccgttcg gtgaatttac cggccactac tccggcgggc   1440
gcaacatgac cgtagtgcgc atcgataaag tctcttaccg caccaaaccg attttttgaat   1500 cgctctatct cggtatgccg tggaccgaaa tcgactacct gatggggcca gccacctgtg   1560
tgccgctgta tcagcaactg aaagccgagt tcccggaagt gcaggcggtg aacgccatgt   1620
acacccacgg cctgctggcg attatctcca ccaaaaaacg ctacggcggc tttgcccgcg   1680
cggtgggcct gcgtgcgatg accacgccgc acggtctggg ctacgtgaag atggtgatta   1740
tggtcgatga agacgttgat ccgttcaacc tgccgcaggt gatgtgggcg cttttcgtcga   1800 aagtgaaccc ggcaggggat ctggtgcagt tgccgaatat gtcagtactg gaactcgacc   1860
ctggctcaag cccggcgggg atcaccgata agctgattat cgacgccact acgcctgtcg   1920
ccccggacaa ccgtggtcac tacagccagc cggtggtgga cttaccggaa accaaagcct   1980
gggctgaaaa actgaccgct atgctggccg cacgtaaata aggagaacaa gatgatttgt   2040
ccacgttgtg ccgatgaaca gattgaagtg atggcgaaat cgccggtgaa agatgtctgg   2100
acggtctacc agtgccagca ttgcctttat acctggcgcg atactgaacc gctacgccgc   2160
accagccgcg aacattaccc gcaagcgttc cgtatgactc aaaaagatat tgatgacgcg   2220
ccaatggtgc cgagcattcc gccgctgctg gcggcagata agcgctaa                2268

<210> SEQ ID NO 21
<211> LENGTH: 2304
<212> TYPE: DNA
<213> ORGANISM: Paenibacillus polymyxa

<400> SEQUENCE: 21
atgaagaaaa tcattgtagg aatatcggga gcgacagggt caatctttgg tatccgtata     60
```

```
ttgcaaaaat tacgggaggc tggagtccaa agccatctgg tgctatcccc gtgggctatt      120
gccaacattc cctatgagac aggctacacg gtgaaggatg tgaaggcaat ggcggatgca      180
gtctactcgt ataaggatca ggccgcacgt atttctagcg gctccttccg ggtagatggt      240
atggtcgtcg ctccttgcag tatgaagact cttgcctcta ttcgtatcgg tatggcggac      300
aacctgctta cccgatcagc ggatgtgata ctgaaggagc gaaagaagct gctgctcatg      360
accagagaaa caccattaag cagtatccat ctggaaaata tgctggagct gtcacgtatg      420
ggcgtgatga tcctgccgcc gatgcctgcc ttttataatc atcctgcaag tatcgaggaa      480
ttagtggatc atattgtttt tcgcgcattg gatcagttcg gtattgtcac aaccgcagcc      540
aaacgctggg atgggatgaa gcagaatgac tccaggctgc accagaattg agaaatcgaa      600
agacgaagga gaatgaatga tggcttataa agactttcgc gattttctac acccttggaa      660
aaaggaggga caattactca cgatcagcga tgaggtaaag ccggagccgg acctcgcagc      720
agctaacaga gcattaaaca atcttggaga taagacgcct gctctctttt tcaacaacat      780
ctatggatat acggatgctc gtattgcaat gaatgtgatg ggctcctggc ccaatcatgc      840
cctcatgatg ggaatgccca aaaatacgcc gctcaaggag cagttttttg aatttgccag      900
acgctatgaa caatttccgg tgcccgtgaa gcgggaagaa gccgctcctt tcatgaagt       960 cgaaattacg gagaatatta atttgtttga tattttgccg ttgtttcgtt tgaatcaggg     1020
ggacggaggg ttttatttgg ataaagcaat tctaatttca cgcgatctgg atgacccgga     1080
cacctacggt aagcaaaatg tcggcttata ccggatgcag gtgaaaggca agaaccgttt     1140
gggcatccag cctgtaccac agcatgatat tgcgatccat atccgtcagg ctgaggagcg     1200
tggcgaaaat ctgaaggtgg ctattgcccc tcggatgtgag cctgtgatta caacggctgc     1260
ttctacgcca ctgctgtacg atcaatccga atatgagatg gcgggcgcca ttcagggcga     1320
gccttatcgt gtggtcaaag cgaaggatgc agatctggat ctgccttggg gagccgaggt     1380
cattttggaa ggcgaagtgt tagcaggtga acgtgagtat gaaggtccat tcggtgaatt     1440
cacaggtcac tattccggcg gtcgcgcgat gccagtcatt cagattaatc gtgtatatca     1500
ccgcaaacag cctatctttg agcatctgta catcgggatg ccttggacgg aaacggatta     1560
tatgatcgat gtgaatacaa gtgtaccgtt gtttcagcag cttaaggatg cttttcctaa     1620
tgaaatcgta gctgttaatg ccatgtatac gcatgggctg gtcgctatta tttccacgaa     1680
aacccggtat ggcggctttg cgaaggctgt gggaatgcgt gcgttaacga ctccgcatgg     1740
attggggtat tgcaagctgg tgattgtggt ggacgaggag gtcgatccgt tcaatctgcc     1800
gcaagtcatg tgggctttat ccaccaagct tcatccaaag catgatgctg tcattgttcc     1860
tggcttgtct attttaccgc ttgacccccgg ctctgatccg gcaggtatga cgcacaaaat     1920
gatactggat gcgacgacac ctgtagcacc ggatattaga ggccattact cgcagccgct     1980
cgattccccg ctgggtgtag cggaatggga gaaaaagttg agccaaatgc ttcgctaaat     2040 attttaaaa acaaagaaaa tttaaaggag tgctgacaga tgcatatttg tccccgttgt     2100
gagtccaatc gttcagaagt cgtttcccat tcgccggtta aggtgcctg ggaggttttg      2160 ttgtgccctg tatgcctgtt cacatggcga acctcagaac cggatagcat tactgatcca     2220
gcaaagtata aatcggcgtt caaggtaaac ccccaagata ttccggatgc tgctcatgtt     2280
cctcctattc cagagcggat atag                                            2304
```

<210> SEQ ID NO 22

```
<211> LENGTH: 2268
<212> TYPE: DNA
<213> ORGANISM: Citrobacter koseri

<400> SEQUENCE: 22
atgagactga ttgtggggat gaccggcgca acggggggcgc cgctaggcat tgcgctgcta      60
caggcgctgc ggcaaatgcc gacagtagaa acacacctgg taatgtctaa gtgggccaaa     120
acgaccattg agctggaaac gccttacagt gcgcgagatg ttgccggact ggctgattac     180
tgccataacc cggcggatca gcggcgacg atctcttccg gctcatttcg caccgacggc      240
atgatcatta tgccttgcag tatgaaaacg ctggcgggga ttcgcgcagg atatgccgag     300
gggttagttg gccgtgccgc cgatgtggtg ctgaaagaag ggcgcaaact ggtgctggtg     360
ccgcgtgaaa tgccgctcag cacgatccat ctggaaaaca tgctcgccct ttcccgcatg     420
ggggtcgcga tggtgccgcc catgcctgct ttctacaacc atccgcaaac tattgatgat     480
attacgcagc atattgtggc gcgtgtgctg atcagtttg gtctggagca tccgcgtgcc      540
cggcgctggc aggggttgca gcaggcgcag aattttttcac aggagaatga ataatggcat     600
ttgatgactt acgcagcttt ttgcaggcgc tcgacgagca ggggcaactg ctgaaaatca     660
gtgaagaagt gaatgcagag ccggatctgg ctgctgcggc taacgcaacc gggcgcattg     720
gcgacggcgc gcctgcgctg tggttcgata atatccgtgg cttcacggat gcgcgcgtgg     780
cgatgaacac cattggttcc tggcagaacc atgccatctc tttaggcttg ccgcctaatg     840
cgccagtaaa aaagcaaatt gatgaattta ccgccgctg gacacgttc cccgtcgccc        900 ccgagcgccg agccaacccg gcgtgggcgg aaaacaccgt tgatggcgag cgatcaacc     960 tgtttgatat tctgccgctg tttcgcctca cgatggcga tggcggcttc tatctggata    1020
aagcctgtgt cgtctcccgc gatccgctcg acccggatca cttcggcaag cagaatgtgg    1080
gtatctaccg gatggaagtg aaaggcaagc gcaagctggg cctgcaaccg gtgccaatgc    1140
acgatatcgc gctgcatctg cataaggcgg aagagcgtgg cgaagatctg ccgattgcta    1200
ttacgctcgg taacgatccg atcatcactc tgatgggcgc cacgccgctg aaatacgatc    1260
agtctgagta tgaaatggcg ggcgcgctgc gcgaaagccc ataccgatc gccaccgcgc     1320 cgctgaccgg ctttgatgtg ccgtgggtt cagaagtgat ccttgaaggg gtgatcgaaa    1380
gccgtaagcg tgaaattgaa gggccgtttg gcgagtttac cggccactat tctggtgggc    1440
gcaatatgac ggtggtgcgc atcgacaaag tgtcttatcg cactaaaccg attttttgaat    1500 cactctatct ggggatgccg tggactgaaa tcgactacct gatggggcca gcgacctgtg    1560
tgccgctgta tcagcagttg aaagcggaat tcccggaagt gcaggcggtt aacgccatgt    1620
atacccacgg tctgctggcg attatctcga ccaaaaaacg ctacggcgga tttgcccgcg    1680
cgatcggcct gcgggcaatg accacgccgc acggtctggg ctatgtgaag atggtgatta    1740
tggttgatga ggatgtcgat ccgttcaacc tgccgcaggt gatgtgggcg ctgtcgtcga    1800
aggtcaaccc ggcaggcgat ctggtgcagc tgccgaacat gtcggtgctg gaactggacc    1860
caggctcaag cccggcgggg atcactgaca aactgatcat cgacgccaca acgccggttg    1920
cgccggataa tcgcggccac tacagccagc cggtatgtga tttaccggaa accaaagcct    1980
gggctgaaaa gctgactgcc atgctggcca accgtaaata aggagtagca gatgatttgt    2040
ccacgttgtg ctgatgaaca tattgaattg atggcgacct ctccggtcaa agggatctgg    2100
acggtgtatc agtgccagca ttgtctgtac acctggcgtg ataccgagcc gctacgccgt    2160
accagccgtg aacattatcc gcaagcgttt cgcatgacgc agaaagatat tgatcaagcg    2220
```

```
ccgatggtgc cgggcattcc accgctgctg gcggaagata agcgttaa        2268
```

<210> SEQ ID NO 23
<211> LENGTH: 2318
<212> TYPE: DNA
<213> ORGANISM: Pantoea ananatis

<400> SEQUENCE: 23

```
atgagtagat tactgttaat ttcattcgta cacgaacgtt atttgcaagg aagtcagatg     60
agaattgtaa tcggtatgac gggagcaaca ggtgcccctt taggggtggc tctgctcagc    120
attttgcagg aaatcaaaga ggttgaaact catctgattt tgagcaagtg ggctaaaacc    180
acaattgaac tcgaaacgcc ttttcatcg cgtgaggtga tgagcatggc tgatgttgtg     240
tatggcccgt ccgaccaggc cgctactctc tcgtcaggtt cttttcacac cgatgggatg    300
gtcattattc cttgcagtat gaaaaccttg gcgggaattc gcatgggata cgcggaaggc    360
cttattggac gggctgctga tgtcgtcatt aaagaaggca gaaaacttgt gctggtcccc    420
agagagacgc ctctcagcac cattcacctg gaaaatatgc tagccctttc ccgtcttggc    480
gtatccatgg ttccgcccat gcccgctttt tataaccacc ccgcagtaat tgatgatgtg    540
atcgatcatg tcgtttctcg tgttctcgac cagtttggga ttgcctcgcc aaaggcaaat    600
cgctggaaag gctgaacaa ttctaagaaa tccctgagta tggagagtaa ataatggctt     660
ttgatgacct acgtagcttc cttaaggctc tggacgagca ggggcagctt cttgagattg    720
atgaagaggt tttacccgaa cctgatattg ccgcggccgc taatgctaca ggccgaattg    780
gtgaaggtgc accggcaatc tcattcaaaa aaataaaggg gttcaatcat gctcatgttg    840
tgatgaacac tattggttcc tggcaaaacc atgcaatttc actgggcctc caatgaata     900
ccccagtgaa acagcagata gatgaattca ttcgtcgctg ggacactttt cctgtggcac    960
cagagcggcg cgacaatgcg ccctggtcag aaaataccgt tgattgtgaa gagatcaatc   1020
tcttcgacat ccttcccctg ttccgcctga cgacggcga cggcggtttc tatcttgata   1080
aggcctgcgt agtatcacgt gacccgcttg atccagaaca tttcggtaag caaaacgtcg   1140
gcatttaccg gatggaggtg aaaggtaaac gtaaactcgg gctccagccc gtgccgatgc   1200
atgacattgc acttcatctc cataaggccg aagaacgcgg cgacgatctg ccagtggcta   1260
ttacgctggg caatgacccc attattacat tgatgggcgc cacgccgctg aaatacgacc   1320
agtcagaata tgagatggca ggtgcgctgc gtgaaagccc gtaccccatc gcctccgcgc   1380
ctctgaccgg ctttgatgtg ccgtggggat cggaagtcat tcttgaaggc gtgatagaag   1440
ggcgcaaacg tgagattgaa ggaccgtttg gcgaattcac cggccattat tccggcggtc   1500
gcaatatgac cgttgtgcgg attgataagg tctcctaccg cactaagcca atattcgagt   1560
cattgtatct gggaatgccc tggaccgaaa ttgattatct gatgggcccg gcaacctgtg   1620
tccctttgta tcaacagctg aaagcggatt ccctgaggt gcaggctgta aatgcaatgt    1680
atacacacgg attactggcc attatttcta caaagaaacg ttatggtgga tttgcccgtg   1740
ctgtaggcgt acgggcgatg acaaccccgc atggtctggg ctacgtcaag atggtgatca   1800
tggtcgatga ggatgtcgat ccctttaacc tgcctcaggt gatgtgggcg ctgtcttcaa   1860
aggtcaatcc gcaaggcgat ctcgttcaac tgccaaacat gtccgtactg aactggacc    1920
cgggttccag ccctgcggga atcacggata aacttgtgat cgatgcgacg actcccgtgg   1980
caccggatac ccgcggccac tacagtcagc cggtaaaaga cctgccagaa acttcaatct   2040
```

-continued

```
gggttgagaa gttaacgtcc ctgttatcaa atcgcggtta aggagaaagt atgatttgtc    2100
cacgttgtgc tgatgaacac attgaaatca tggcaacatc cccagttgag gggatatgga    2160
cggtgcatca gtgtcagcat tgcctgtaca catggcgcaa tacagagcca gcccgaagaa    2220
cggagcggga acattatcct gaagccttcc ggatgactca acgtgatatt gataatgcgc    2280
cggaagtccc gtctgtccct cctctgttag ctaagtaa                            2318
```

<210> SEQ ID NO 24
<211> LENGTH: 26
<212> TYPE: DNA
<213> ORGANISM: Artificial Sequence
<220> FEATURE:
<223> OTHER INFORMATION: Amplification Primer

<400> SEQUENCE: 24
ctctcatatg acagcatcac cttggg                                         26

<210> SEQ ID NO 25
<211> LENGTH: 32
<212> TYPE: DNA
<213> ORGANISM: Artificial Sequence
<220> FEATURE:
<223> OTHER INFORMATION: Amplification Primer

<400> SEQUENCE: 25
ctctcatatg tcatcttaac gacgctccat tc                                  32

<210> SEQ ID NO 26
<211> LENGTH: 36
<212> TYPE: DNA
<213> ORGANISM: Artificial Sequence
<220> FEATURE:
<223> OTHER INFORMATION: Amplification Primer

<400> SEQUENCE: 26
ggaattccat atgaagcgaa ttgttgtcgg aattac                              36

<210> SEQ ID NO 27
<211> LENGTH: 34
<212> TYPE: DNA
<213> ORGANISM: Artificial Sequence
<220> FEATURE:
<223> OTHER INFORMATION: Amplification Primer

<400> SEQUENCE: 27
ggaattccat atgctacttc ggctgctcat catc                                34

<210> SEQ ID NO 28
<211> LENGTH: 35
<212> TYPE: DNA
<213> ORGANISM: Artificial Sequence
<220> FEATURE:
<223> OTHER INFORMATION: Amplification Primer

<400> SEQUENCE: 28
ggaattccat atggcagaac aaccatggga tttac                               35

<210> SEQ ID NO 29
<211> LENGTH: 34
<212> TYPE: DNA
<213> ORGANISM: Artificial Sequence
<220> FEATURE:
<223> OTHER INFORMATION: Amplification Primer

<400> SEQUENCE: 29

```
ggaattccat atggacggca taactaatcg catc                              34

<210> SEQ ID NO 30
<211> LENGTH: 31
<212> TYPE: DNA
<213> ORGANISM: Artificial Sequence
<220> FEATURE:
<223> OTHER INFORMATION: Amplification Primer

<400> SEQUENCE: 30
ctctcatatg aaacgaattg ttgtgggaat c                                 31

<210> SEQ ID NO 31
<211> LENGTH: 26
<212> TYPE: DNA
<213> ORGANISM: Artificial Sequence
<220> FEATURE:
<223> OTHER INFORMATION: Amplification Primer

<400> SEQUENCE: 31
ctctcatatg ctaccgcggt tgctcg                                       26

<210> SEQ ID NO 32
<211> LENGTH: 26
<212> TYPE: DNA
<213> ORGANISM: Artificial Sequence
<220> FEATURE:
<223> OTHER INFORMATION: Amplification Primer

<400> SEQUENCE: 32
ctctcatatg gcagaacaac catggg                                       26

<210> SEQ ID NO 33
<211> LENGTH: 34
<212> TYPE: DNA
<213> ORGANISM: Artificial Sequence
<220> FEATURE:
<223> OTHER INFORMATION: Amplification Primer

<400> SEQUENCE: 33
ctctcatatg ttacttcaaa tacttctccc agtc                              34

<210> SEQ ID NO 34
<211> LENGTH: 36
<212> TYPE: DNA
<213> ORGANISM: Artificial Sequence
<220> FEATURE:
<223> OTHER INFORMATION: Amplification Primer

<400> SEQUENCE: 34
agttgagaca tatgggtgaa gacaaatggg atttgc                            36

<210> SEQ ID NO 35
<211> LENGTH: 34
<212> TYPE: DNA
<213> ORGANISM: Artificial Sequence
<220> FEATURE:
<223> OTHER INFORMATION: Amplification Primer

<400> SEQUENCE: 35
ttattttaca tatgtcatct gccatcccaa cgtg                              34

<210> SEQ ID NO 36
<211> LENGTH: 40
<212> TYPE: DNA
```

<213> ORGANISM: Artificial Sequence
<220> FEATURE:
<223> OTHER INFORMATION: Amplification Primer

<400> SEQUENCE: 36
aggtcatcat atgtcagatt attatgattt gagacgggtc     40

<210> SEQ ID NO 37
<211> LENGTH: 34
<212> TYPE: DNA
<213> ORGANISM: Artificial Sequence
<220> FEATURE:
<223> OTHER INFORMATION: Amplification Primer

<400> SEQUENCE: 37
acgtggcgca tatggtcatc attaccctcc cgtc     34

<210> SEQ ID NO 38
<211> LENGTH: 44
<212> TYPE: DNA
<213> ORGANISM: Artificial Sequence
<220> FEATURE:
<223> OTHER INFORMATION: Amplification Primer

<400> SEQUENCE: 38
gaggcccggg atgacagaac aaccatatga tttaagaaaa gtac     44

<210> SEQ ID NO 39
<211> LENGTH: 30
<212> TYPE: DNA
<213> ORGANISM: Artificial Sequence
<220> FEATURE:
<223> OTHER INFORMATION: Amplification Primer

<400> SEQUENCE: 39
actccccggg ctaaacgcgg ttgttcacac     30

<210> SEQ ID NO 40
<211> LENGTH: 41
<212> TYPE: DNA
<213> ORGANISM: Artificial Sequence
<220> FEATURE:
<223> OTHER INFORMATION: Amplification Primer

<400> SEQUENCE: 40
aggcagtact atgagtgaac aaccttatga tttacgtaaa g     41

<210> SEQ ID NO 41
<211> LENGTH: 36
<212> TYPE: DNA
<213> ORGANISM: Artificial Sequence
<220> FEATURE:
<223> OTHER INFORMATION: Amplification Primer

<400> SEQUENCE: 41
atgaagtact ttatttagca taggtaacca cttggg     36

<210> SEQ ID NO 42
<211> LENGTH: 32
<212> TYPE: DNA
<213> ORGANISM: Artificial Sequence
<220> FEATURE:
<223> OTHER INFORMATION: Amplification Primer

<400> SEQUENCE: 42
ctctcatatg aaaatagctg taggaatcac ag     32

<210> SEQ ID NO 43
<211> LENGTH: 29
<212> TYPE: DNA
<213> ORGANISM: Artificial Sequence
<220> FEATURE:
<223> OTHER INFORMATION: Amplification Primer

<400> SEQUENCE: 43
ctctcatatg ttaagatcgg ggtggcaca                              29

<210> SEQ ID NO 44
<211> LENGTH: 28
<212> TYPE: DNA
<213> ORGANISM: Artificial Sequence
<220> FEATURE:
<223> OTHER INFORMATION: Amplification Primer

<400> SEQUENCE: 44
ctctcatatg aacatcatcg tcggaatc                               28

<210> SEQ ID NO 45
<211> LENGTH: 33
<212> TYPE: DNA
<213> ORGANISM: Artificial Sequence
<220> FEATURE:
<223> OTHER INFORMATION: Amplification Primer

<400> SEQUENCE: 45
ctctcatatg ttagattttc cggtctggaa tcg                         33

<210> SEQ ID NO 46
<211> LENGTH: 28
<212> TYPE: DNA
<213> ORGANISM: Artificial Sequence
<220> FEATURE:
<223> OTHER INFORMATION: Amplification Primer

<400> SEQUENCE: 46
ctctcatatg aaactcgttg tcgggatg                               28

<210> SEQ ID NO 47
<211> LENGTH: 26
<212> TYPE: DNA
<213> ORGANISM: Artificial Sequence
<220> FEATURE:
<223> OTHER INFORMATION: Amplification Primer

<400> SEQUENCE: 47
ctctcatatg tcaggccttt ctttcc                                 26

<210> SEQ ID NO 48
<211> LENGTH: 37
<212> TYPE: DNA
<213> ORGANISM: Artificial Sequence
<220> FEATURE:
<223> OTHER INFORMATION: Amplification Primer

<400> SEQUENCE: 48
agtatgattc atatgaaagc agaattcaag cgtaaag                     37

<210> SEQ ID NO 49
<211> LENGTH: 30
<212> TYPE: DNA
<213> ORGANISM: Artificial Sequence
<220> FEATURE:

<223> OTHER INFORMATION: Amplification Primer

<400> SEQUENCE: 49
acatacagtt catatggatc aagcctttcg                                    30

<210> SEQ ID NO 50
<211> LENGTH: 32
<212> TYPE: DNA
<213> ORGANISM: Artificial Sequence
<220> FEATURE:
<223> OTHER INFORMATION: Amplification Primer

<400> SEQUENCE: 50
ctctcatatg aaagcagaat tcaagcgtaa ag                                 32

<210> SEQ ID NO 51
<211> LENGTH: 28
<212> TYPE: DNA
<213> ORGANISM: Artificial Sequence
<220> FEATURE:
<223> OTHER INFORMATION: Amplification Primer

<400> SEQUENCE: 51
ctctcatatg tcaagccttt cgttccgg                                      28

<210> SEQ ID NO 52
<211> LENGTH: 32
<212> TYPE: DNA
<213> ORGANISM: Artificial Sequence
<220> FEATURE:
<223> OTHER INFORMATION: Amplification Primer

<400> SEQUENCE: 52
ctctcatatg aaactgatta ttgggatgac cg                                 32

<210> SEQ ID NO 53
<211> LENGTH: 29
<212> TYPE: DNA
<213> ORGANISM: Artificial Sequence
<220> FEATURE:
<223> OTHER INFORMATION: Amplification Primer

<400> SEQUENCE: 53
ctctcatatg ttaacgctta tctgccgcc                                     29

<210> SEQ ID NO 54
<211> LENGTH: 30
<212> TYPE: DNA
<213> ORGANISM: Artificial Sequence
<220> FEATURE:
<223> OTHER INFORMATION: Amplification Primer

<400> SEQUENCE: 54
ctctcatatg agattgatcg tgggaatgac                                    30

<210> SEQ ID NO 55
<211> LENGTH: 30
<212> TYPE: DNA
<213> ORGANISM: Artificial Sequence
<220> FEATURE:
<223> OTHER INFORMATION: Amplification Primer

<400> SEQUENCE: 55
ctctcatatg ttacagcaat ggcggaatgg                                    30

```
<210> SEQ ID NO 56
<211> LENGTH: 30
<212> TYPE: DNA
<213> ORGANISM: Artificial Sequence
<220> FEATURE:
<223> OTHER INFORMATION: Amplification Primer

<400> SEQUENCE: 56
ctctcatatg aggctaattg tcggaatgac                                   30

<210> SEQ ID NO 57
<211> LENGTH: 29
<212> TYPE: DNA
<213> ORGANISM: Artificial Sequence
<220> FEATURE:
<223> OTHER INFORMATION: Amplification Primer

<400> SEQUENCE: 57
ctctcatatg ttaacgctta ccatccgcc                                    29

<210> SEQ ID NO 58
<211> LENGTH: 30
<212> TYPE: DNA
<213> ORGANISM: Artificial Sequence
<220> FEATURE:
<223> OTHER INFORMATION: Amplification Primer

<400> SEQUENCE: 58
ctctcatatg agattgattg tgggaatgac                                   30

<210> SEQ ID NO 59
<211> LENGTH: 31
<212> TYPE: DNA
<213> ORGANISM: Artificial Sequence
<220> FEATURE:
<223> OTHER INFORMATION: Amplification Primer

<400> SEQUENCE: 59
ctctcatatg gagtctggtt tagttctctg c                                 31

<210> SEQ ID NO 60
<211> LENGTH: 28
<212> TYPE: DNA
<213> ORGANISM: Artificial Sequence
<220> FEATURE:
<223> OTHER INFORMATION: Amplification Primer

<400> SEQUENCE: 60
ctctcatatg aaactgatcg tcgggatg                                     28

<210> SEQ ID NO 61
<211> LENGTH: 28
<212> TYPE: DNA
<213> ORGANISM: Artificial Sequence
<220> FEATURE:
<223> OTHER INFORMATION: Amplification Primer

<400> SEQUENCE: 61
ctctcatatg ttagcgctta ccttccgc                                     28

<210> SEQ ID NO 62
<211> LENGTH: 27
<212> TYPE: DNA
<213> ORGANISM: Artificial Sequence
<220> FEATURE:
<223> OTHER INFORMATION: Amplification Primer
```

```
<400> SEQUENCE: 62
ctctcatatg agactgatcg tcgggat                                          27

<210> SEQ ID NO 63
<211> LENGTH: 28
<212> TYPE: DNA
<213> ORGANISM: Artificial Sequence
<220> FEATURE:
<223> OTHER INFORMATION: Amplification Primer

<400> SEQUENCE: 63
ctctcatatg ttagcgctta tctgccgc                                         28

<210> SEQ ID NO 64
<211> LENGTH: 35
<212> TYPE: DNA
<213> ORGANISM: Artificial Sequence
<220> FEATURE:
<223> OTHER INFORMATION: Amplification Primer

<400> SEQUENCE: 64
ctctcatatg aagaaaatca ttgtaggaat atcgg                                 35

<210> SEQ ID NO 65
<211> LENGTH: 31
<212> TYPE: DNA
<213> ORGANISM: Artificial Sequence
<220> FEATURE:
<223> OTHER INFORMATION: Amplification Primer

<400> SEQUENCE: 65
ctctcatatg ctatatccgc tctggaatag g                                     31

<210> SEQ ID NO 66
<211> LENGTH: 28
<212> TYPE: DNA
<213> ORGANISM: Artificial Sequence
<220> FEATURE:
<223> OTHER INFORMATION: Amplification Primer

<400> SEQUENCE: 66
ctctcatatg agactgattg tggggatg                                         28

<210> SEQ ID NO 67
<211> LENGTH: 31
<212> TYPE: DNA
<213> ORGANISM: Artificial Sequence
<220> FEATURE:
<223> OTHER INFORMATION: Amplification Primer

<400> SEQUENCE: 67
ctctcatatg ttaacgctta tcttccgcca g                                     31

<210> SEQ ID NO 68
<211> LENGTH: 38
<212> TYPE: DNA
<213> ORGANISM: Artificial Sequence
<220> FEATURE:
<223> OTHER INFORMATION: Amplification Primer

<400> SEQUENCE: 68
ctctcatatg agtagattac tgttaatttc attcgtac                              38

<210> SEQ ID NO 69
<211> LENGTH: 32
```

```
<212> TYPE: DNA
<213> ORGANISM: Artificial Sequence
<220> FEATURE:
<223> OTHER INFORMATION: Amplification Primer

<400> SEQUENCE: 69
ctctcatatg ttacttagct aacagaggag gg                              32

<210> SEQ ID NO 70
<211> LENGTH: 30
<212> TYPE: DNA
<213> ORGANISM: Artificial Sequence
<220> FEATURE:
<223> OTHER INFORMATION: Amplification Primer

<400> SEQUENCE: 70
ctctctgcag catcgttgct gaatgtccag                                 30

<210> SEQ ID NO 71
<211> LENGTH: 21
<212> TYPE: DNA
<213> ORGANISM: Artificial Sequence
<220> FEATURE:
<223> OTHER INFORMATION: Amplification Primer

<400> SEQUENCE: 71
gatcaacgat ctgttcagct g                                          21

<210> SEQ ID NO 72
<211> LENGTH: 40
<212> TYPE: DNA
<213> ORGANISM: Artificial Sequence
<220> FEATURE:
<223> OTHER INFORMATION: Amplification Primer

<400> SEQUENCE: 72
agctgaacag atcgttgatc agaactgatc ctgcaccctg                      40

<210> SEQ ID NO 73
<211> LENGTH: 30
<212> TYPE: DNA
<213> ORGANISM: Artificial Sequence
<220> FEATURE:
<223> OTHER INFORMATION: Amplification Primer

<400> SEQUENCE: 73
ctctgagctc gttgatgtca atgcgcagag                                 30
```